US00RE43824E

(19) United States
(12) Reissued Patent
Sheldrake et al.

(10) Patent Number: US RE43,824 E
(45) Date of Reissued Patent: Nov. 20, 2012

(54) NEEDLELESS SYRINGE

(75) Inventors: Colin D. Sheldrake, Wiltshire (GB); George Costigan, Oxfordshire (GB); Brian J. Bellhouse, East Sussex (GB)

(73) Assignee: Powder Pharmaceuticals Inc., Hong Kong (HK)

(21) Appl. No.: 13/077,571

(22) Filed: Mar. 31, 2011

Related U.S. Patent Documents

Reissue of:
(64) Patent No.: 7,547,292
Issued: Jun. 16, 2009
Appl. No.: 10/466,076
PCT Filed: Jan. 11, 2002
PCT No.: PCT/GB02/00114
§ 371 (c)(1),
(2), (4) Date: Dec. 23, 2003
PCT Pub. No.: WO02/055139
PCT Pub. Date: Jul. 18, 2002

(30) Foreign Application Priority Data

Jan. 11, 2001 (GB) ..... 0100756.6

(51) Int. Cl.
*A61M 5/30* (2006.01)
(52) U.S. Cl. ..... 604/68; 604/72
(58) Field of Classification Search ..... 604/68–72, 604/48, 131, 140, 142, 147
See application file for complete search history.

(56) References Cited

U.S. PATENT DOCUMENTS 2,307,986 A 1/1943 Brown et al.
3,674,028 A 7/1972 Ogle
4,133,163 A 1/1979 Wilson
4,478,368 A 10/1984 Yie
4,555,872 A 12/1985 Yie
4,586,854 A 5/1986 Newman et al.
4,587,772 A 5/1986 Griffiths
4,615,649 A 10/1986 Sharpless
4,624,080 A 11/1986 Jakobsson
4,631,871 A 12/1986 Saunders
(Continued)

FOREIGN PATENT DOCUMENTS

CN 1284383 2/2001
(Continued)

OTHER PUBLICATIONS

Yu et al., "Particle Acceleration for Delivery Deoxyribonucleic Acid Vaccine into Skin In Vivo", *Review of Scientific Instruments*, vol. 72, No. 8, pp. 3390-3395, American Institute of Physics, Aug. 2001.

(Continued)

*Primary Examiner* — Kevin C Sirmons
*Assistant Examiner* — Andrew Gilbert
(74) *Attorney, Agent, or Firm* — Levine Bagade Han LLP

(57) ABSTRACT

A method of distributing particles in a flow of gas and a needleless syringe for use in the needleless injection of particles into the skin or mucosa of a vertebrate subject are disclosed. The syringe includes a convergence which reduces pressure of the gas flowing in the gas flow path due to the Venturi effect such that particles initially located outside of the gas flow path are drawn into the gas flow path under the action of the reduced pressure and become entrained in the gas. An exit nozzle accelerates the particles so entrained. In another aspect of the invention, there is provided a method of creating a gas flow in a needleless syringe which comprises flowing gas through a first convergence into a chamber to form a transsonic gas jet in the chamber and passing the gas jet from the chamber into a second convergence and along the nozzle.

23 Claims, 13 Drawing Sheets

U.S. PATENT DOCUMENTS

| | | | |
|---|---|---|---|
| 4,648,215 | A | 3/1987 | Hashish et al. |
| 4,663,893 | A | 5/1987 | Savanick et al. |
| 4,666,083 | A | 5/1987 | Yie |
| 4,668,190 | A | 5/1987 | Overmyer |
| 4,674,491 | A | 6/1987 | Brugger et al. |
| 4,708,214 | A | 11/1987 | Krawza et al. |
| 4,711,056 | A | 12/1987 | Herrington et al. |
| 4,715,535 | A | 12/1987 | Mulder |
| D299,536 | S | 1/1989 | Robbins |
| 4,807,814 | A | 2/1989 | Douche et al. |
| 4,809,706 | A | 3/1989 | Watson et al. |
| 4,817,874 | A | 4/1989 | Jarzebowicz |
| 4,829,724 | A | 5/1989 | Miller et al. |
| 4,913,699 | A | 4/1990 | Parsons |
| 4,934,111 | A | 6/1990 | Hashish et al. |
| 4,941,298 | A | 7/1990 | Fernwood et al. |
| 4,945,688 | A | 8/1990 | Yie |
| 4,951,429 | A | 8/1990 | Hashish et al. |
| 5,024,656 | A | 6/1991 | Gasaway et al. |
| 5,037,247 | A | 8/1991 | Kaiser et al. |
| 5,054,249 | A | 10/1991 | Rankin |
| 5,100,792 | A | 3/1992 | Sanford et al. |
| 5,155,946 | A | 10/1992 | Domann |
| 5,283,985 | A | 2/1994 | Browning |
| 5,301,878 | A | 4/1994 | Sinclair et al. |
| 5,312,335 | A | 5/1994 | McKinnon et al. |
| 5,312,577 | A | 5/1994 | Peterson et al. |
| 5,325,638 | A | 7/1994 | Lynn |
| D349,958 | S | 8/1994 | Hollis et al. |
| 5,335,459 | A | 8/1994 | Dale |
| 5,365,762 | A | 11/1994 | Thompson |
| 5,366,560 | A | 11/1994 | Rubey et al. |
| 5,383,851 | A | 1/1995 | McKinnon et al. |
| 5,473,947 | A | 12/1995 | Buquet |
| 5,503,627 | A | 4/1996 | McKinnon et al. |
| 5,505,566 | A | 4/1996 | Gruber |
| 5,514,026 | A | 5/1996 | Schaffer |
| 5,533,501 | A | 7/1996 | Denyer |
| 5,551,909 | A | 9/1996 | Bailey |
| 5,571,323 | A | 11/1996 | Duffy et al. |
| 5,584,807 | A | 12/1996 | McCabe |
| 5,588,901 | A | 12/1996 | Rubey et al. |
| 5,615,980 | A | 4/1997 | Mauchle |
| 5,616,067 | A | 4/1997 | Goenka |
| 5,630,796 | A | 5/1997 | Bellhouse et al. |
| 5,643,058 | A | 7/1997 | Erichsen et al. |
| 5,645,380 | A | 7/1997 | Rutz |
| 5,718,581 | A | 2/1998 | Fernwood et al. |
| 5,749,684 | A | 5/1998 | Horn Feja |
| D399,951 | S | 10/1998 | Drach |
| 5,860,598 | A | 1/1999 | Cruz |
| 5,865,796 | A | 2/1999 | McCabe |
| 5,873,680 | A | 2/1999 | Huber et al. |
| 5,876,267 | A | 3/1999 | Kanda |
| 5,893,397 | A | 4/1999 | Peterson et al. |
| 5,899,880 | A | 5/1999 | Bellhouse et al. |
| 5,906,858 | A | 5/1999 | Huber et al. |
| 5,951,531 | A | 9/1999 | Ferdman et al. |
| 5,954,232 | A | 9/1999 | Shervington et al. |
| 5,984,677 | A | 11/1999 | Fernwood et al. |
| 5,992,772 | A | 11/1999 | Hibner et al. |
| 6,004,286 | A | 12/1999 | Bellhouse et al. |
| 6,010,478 | A | 1/2000 | Bellhouse et al. |
| 6,012,653 | A | 1/2000 | Gunther et al. |
| 6,013,050 | A | 1/2000 | Bellhouse et al. |
| 6,040,004 | A | 3/2000 | Matsumoto et al. |
| 6,051,274 | A | 4/2000 | Huber et al. |
| 6,053,889 | A | 4/2000 | Heinzen et al. |
| 6,090,790 | A | 7/2000 | Eriksson |
| 6,093,021 | A | 7/2000 | Rainey |
| 6,132,395 | A | 10/2000 | Landau et al. |
| 6,168,587 | B1 | 1/2001 | Bellhouse et al. |
| 6,196,269 | B1 | 3/2001 | Michael et al. |
| 6,203,186 | B1 | 3/2001 | Cruz |
| 6,217,654 | B1 | 4/2001 | Mauchle et al. |
| 6,230,703 | B1 | 5/2001 | Bono |
| 6,280,302 | B1 | 8/2001 | Hashish et al. |
| 6,328,714 | B1 | 12/2001 | Bellhouse et al. |
| 6,475,181 | B1 | 11/2002 | Potter et al. |
| 6,592,545 | B1 | 7/2003 | Bellhouse et al. |
| 6,607,510 | B2 | 8/2003 | Landau |
| 6,613,360 | B1 | 9/2003 | Maa |
| 6,685,669 | B2 | 2/2004 | Bellhouse et al. |
| D488,862 | S | 4/2004 | McCalmon et al. |
| 6,737,101 | B2 | 5/2004 | Maa |
| 6,752,780 | B2 | 6/2004 | Stout et al. |
| 6,770,054 | B1 | 8/2004 | Smolyarov et al. |
| 6,802,826 | B1 | 10/2004 | Smoliarov et al. |
| 6,849,060 | B1 | 2/2005 | Brooks et al. |
| 6,881,200 | B2 | 4/2005 | Bellhouse et al. |
| 6,883,222 | B2 | 4/2005 | Landau |
| 6,893,664 | B1 | 5/2005 | Burkoth et al. |
| 6,987,228 | B1 | 1/2006 | MacMichael et al. |
| 7,029,457 | B2 | 4/2006 | Rogatchev et al. |
| 7,060,048 | B1 | 6/2006 | Nat et al. |
| 7,074,210 | B2 | 7/2006 | Leon et al. |
| 7,182,748 | B1 | 2/2007 | Potter et al. |
| 7,229,645 | B2 | 6/2007 | Maa et al. |
| 7,255,865 | B2 | 8/2007 | Walker |
| 7,358,451 | B2 | 4/2008 | MacMichael et al. |
| 7,479,281 | B1 | 1/2009 | Walker |
| 7,547,292 | B2 | 6/2009 | Sheldrake et al. |
| 7,547,293 | B2 | 6/2009 | Williamson et al. |
| 7,618,394 | B2 | 11/2009 | Bellhouse et al. |
| 7,868,260 | B2 | 1/2011 | MacMichael et al. |
| 7,909,793 | B2 | 3/2011 | Kendall |
| 7,942,846 | B2 | 5/2011 | Bellhouse et al. |
| 8,061,006 | B2 | 11/2011 | Kendall et al. |
| 2001/0003351 | A1 | 6/2001 | Chen et al. |
| 2001/0004681 | A1 | 6/2001 | Landau |
| 2001/0036801 | A1 | 11/2001 | Taylor |
| 2002/0000477 | A1 | 1/2002 | Hara |
| 2002/0087117 | A1 | 7/2002 | Stout et al. |
| 2002/0091353 | A1 | 7/2002 | Bellhouse et al. |
| 2002/0123717 | A1 | 9/2002 | Landau |
| 2002/0123718 | A1 | 9/2002 | Landau |
| 2002/0188249 | A1 | 12/2002 | Landau |
| 2002/0188250 | A1 | 12/2002 | Landau et al. |
| 2002/0188251 | A1 | 12/2002 | Staylor et al. |
| 2003/0019558 | A1 | 1/2003 | Smith et al. |
| 2003/0065286 | A1 | 4/2003 | Landau |
| 2003/0093030 | A1 | 5/2003 | Landau |
| 2003/0163111 | A1 | 8/2003 | Daellenbach |
| 2003/0225368 | A1 | 12/2003 | Landau et al. |
| 2004/0074076 | A1 | 4/2004 | Landau |
| 2004/0111054 | A1 | 6/2004 | Landau et al. |
| 2004/0111055 | A1 | 6/2004 | Daellenbach |
| 2004/0158197 | A1 | 8/2004 | Bellhouse et al. |
| 2004/0159364 | A1 | 8/2004 | Landau et al. |
| 2004/0199106 | A1 | 10/2004 | Landau et al. |
| 2004/0215135 | A1 | 10/2004 | Sheldrake et al. |
| 2005/0010168 | A1 | 1/2005 | Kendall |
| 2005/0027239 | A1 | 2/2005 | Stout et al. |
| 2005/0075601 | A1 | 4/2005 | Landau et al. |
| 2005/0119608 | A1 | 6/2005 | Landau et al. |
| 2005/0191361 | A1 | 9/2005 | O'Connor et al. |
| 2005/0209553 | A1 | 9/2005 | Landau |
| 2005/0209554 | A1 | 9/2005 | Landau |
| 2005/0214227 | A1 | 9/2005 | Prestrelski et al. |
| 2005/0271733 | A1 | 12/2005 | Burkoth et al. |
| 2006/0089593 | A1 | 4/2006 | Landau et al. |
| 2006/0089594 | A1 | 4/2006 | Landau |
| 2006/0171953 | A1 | 8/2006 | Cabezon-Silva et al. |
| 2008/0071211 | A1 | 3/2008 | Williamson et al. |
| 2008/0086079 | A1 | 4/2008 | Williamson et al. |
| 2008/0161755 | A1 | 7/2008 | Landau |
| 2008/0171968 | A1 | 7/2008 | Stout et al. |
| 2008/0262417 | A1 | 10/2008 | Kendall et al. |
| 2008/0300535 | A1 | 12/2008 | Kendall et al. |
| 2009/0137948 | A1 | 5/2009 | Marshall et al. |
| 2009/0137949 | A1 | 5/2009 | Landau et al. |
| 2009/0156992 | A1 | 6/2009 | Landau |
| 2010/0173005 | A1 | 7/2010 | Prestrelski et al. |
| 2010/0298767 | A1 | 11/2010 | Bates et al. |

FOREIGN PATENT DOCUMENTS

| | | | |
|---|---|---|---|
| CN | 1284383 | A | 2/2001 |
| DE | 3204582 | | 8/1983 |
| DE | 3326602 | | 3/1984 |
| DE | 3326602 | A | 3/1984 |
| DE | 3516103 | | 11/1986 |
| DE | 3516103 | A | 11/1986 |
| DE | 3531927 | | 3/1987 |
| DE | 3531927 | A | 3/1987 |
| DE | 3612473 | | 10/1987 |
| DE | 3612473 | C | 10/1987 |
| DE | 3634700 | | 4/1988 |
| DE | 3634700 | A | 4/1988 |
| DE | 3727441 | | 3/1989 |
| DE | 3727441 | A | 3/1989 |
| DE | 3805531 | | 8/1989 |
| DE | 3805531 | A | 8/1989 |
| DE | 4040227 | | 6/1992 |
| DE | 4040227 | A | 6/1992 |
| DE | 4209353 | | 9/1993 |
| DE | 4209353 | C | 9/1993 |
| DE | 9307454 | U | 12/1993 |
| DE | 19937454 | | 12/1993 |
| DE | 4313704 | | 11/1994 |
| DE | 4313704 | C | 11/1994 |
| DE | 4322111 | | 1/1995 |
| DE | 4322111 | C | 1/1995 |
| DE | 4329931 | | 3/1995 |
| DE | 29905035 | | 7/1995 |
| DE | 29603662 | | 8/1996 |
| DE | 29603662 | U | 8/1996 |
| DE | 19541310 | | 5/1997 |
| DE | 19541310 | A | 5/1997 |
| DE | 19600450 | | 7/1997 |
| DE | 19600450 | C | 7/1997 |
| DE | 19729549 | | 1/1999 |
| DE | 19729549 | A | 1/1999 |
| DE | 29905035 | U | 7/1999 |
| DE | 19804233 | | 8/1999 |
| DE | 19804233 | A | 8/1999 |
| DE | 19807917 | | 8/1999 |
| DE | 19807917 | A | 8/1999 |
| DE | 19838276 | | 2/2000 |
| DE | 19838276 | A | 2/2000 |
| DE | 20010854 | | 10/2000 |
| DE | 20010854 | U | 10/2000 |
| DE | 29923669 | | 5/2001 |
| DE | 29923669 | U | 5/2001 |
| DE | 19961202 | | 7/2001 |
| DE | 19961202 | C | 7/2001 |
| DE | 20106816 | | 8/2001 |
| DE | 20106861 | U | 8/2001 |
| DE | 10017556 | | 10/2001 |
| DE | 10017556 | A | 10/2001 |
| EP | 0119338 | | 9/1984 |
| EP | 0119338 | A | 9/1984 |
| EP | 0197625 | | 10/1986 |
| EP | 0295917 | | 12/1988 |
| EP | 0427457 | | 5/1991 |
| EP | 0445104 | | 9/1991 |
| EP | 0445104 | A | 9/1991 |
| EP | 0458685 | B | 11/1991 |
| EP | 04458685 | | 11/1991 |
| EP | 0469814 | | 2/1992 |
| EP | 0471323 | | 2/1992 |
| EP | 0471323 | B | 2/1992 |
| EP | 0515449 | | 12/1992 |
| EP | 0515449 | B | 12/1992 |
| EP | 0518561 | | 12/1992 |
| EP | 0 525 720 | A | 2/1993 |
| EP | 0525720 | | 2/1993 |
| EP | 0621078 | | 10/1994 |
| EP | 0621078 | A | 10/1994 |
| EP | 0629451 | | 12/1994 |
| EP | 0629451 | A | 12/1994 |
| EP | 0651663 | | 5/1995 |
| EP | 0725720 | | 11/1995 |
| EP | 0711609 | | 5/1996 |
| EP | 0711609 | B | 5/1996 |
| EP | 0782866 | B | 7/1997 |
| EP | 0783879 | | 7/1997 |
| EP | 0872866 | | 7/1997 |
| EP | 0880997 | | 12/1998 |
| EP | 0880997 | A | 12/1998 |
| EP | 1011763 | | 6/2000 |
| EP | 1038674 | | 9/2000 |
| EP | 1038674 | A | 9/2000 |
| EP | 1202762 | | 5/2002 |
| EP | 1229950 | | 8/2002 |
| EP | 1267962 | | 1/2003 |
| EP | 1365823 | | 12/2003 |
| EP | 1443985 | | 8/2004 |
| EP | 1485151 | | 12/2004 |
| EP | 1551476 | | 7/2005 |
| EP | 1636090 | | 3/2006 |
| EP | 1745814 | | 1/2007 |
| EP | 1748811 | | 2/2007 |
| EP | 1866012 | | 12/2007 |
| EP | 1979022 | | 10/2008 |
| EP | 2068978 | | 6/2009 |
| EP | 2076301 | | 7/2009 |
| EP | 2092947 | | 8/2009 |
| FR | 2534983 | | 4/1984 |
| FR | 2534983 | B | 4/1984 |
| FR | 2565877 | | 12/1985 |
| FR | 2565877 | B | 12/1985 |
| FR | 2580191 | | 10/1986 |
| FR | 2580191 | B | 10/1986 |
| FR | 2602447 | | 2/1988 |
| FR | 2602447 | B | 2/1988 |
| FR | 2604093 | | 3/1988 |
| FR | 2604093 | B | 3/1988 |
| FR | 2645062 | | 10/1990 |
| FR | 2645062 | B | 10/1990 |
| FR | 2666753 | | 3/1992 |
| FR | 2666753 | B | 3/1992 |
| FR | 2759121 | | 8/1998 |
| FR | 2759121 | B | 8/1998 |
| GB | 2189843 | | 11/1987 |
| GB | 2189843 | B | 11/1987 |
| GB | EP0525720 | A1 * | 3/1991 |
| WO | WO 92/19384 | | 11/1992 |
| WO | WO 93/23225 | | 11/1993 |
| WO | WO 94/02188 | | 2/1994 |
| WO | WO 94/24263 | | 10/1994 |
| WO | WO 94/24263 | A | 10/1994 |
| WO | WO 95/19799 | | 7/1995 |
| WO | WO 95/19799 | A | 7/1995 |
| WO | WO 95/24176 | | 9/1995 |
| WO | WO 96/04947 | | 2/1996 |
| WO | WO 96/04947 | A | 2/1996 |
| WO | WO 96/12513 | | 5/1996 |
| WO | WO 96/20022 | | 7/1996 |
| WO | WO 97/34652 | | 9/1997 |
| WO | WO 97/40963 | | 11/1997 |
| WO | WO 97/47730 | | 12/1997 |
| WO | WO 97/49525 | | 12/1997 |
| WO | WO 98/22639 | | 5/1998 |
| WO | WO 98/48873 | | 11/1998 |
| WO | WO 98/52632 | | 11/1998 |
| WO | WO 98/57691 | | 12/1998 |
| WO | WO 99/49216 | | 9/1999 |
| WO | WO 00/33899 | | 6/2000 |
| WO | WO 00/48654 | | 8/2000 |
| WO | WO 00/58147 | | 10/2000 |
| WO | WO 01/13975 | | 3/2001 |
| WO | WO 01/13977 | | 3/2001 |
| WO | WO 01/33176 | | 5/2001 |
| WO | WO 01/36159 | | 5/2001 |
| WO | WO 01/74425 | | 10/2001 |
| WO | WO 02/055139 | | 7/2002 |
| WO | WO 02/070051 | | 9/2002 |
| WO | WO 02/098479 | | 12/2002 |
| WO | WO 03/011379 | | 2/2003 |
| WO | WO 03/011380 | | 2/2003 |
| WO | WO 03/041762 | | 5/2003 |
| WO | WO 03/072170 | | 9/2003 |
| WO | WO 03/103752 | | 12/2003 |

| | | |
|---|---|---|
| WO | WO 2004/035107 | 4/2004 |
| WO | WO 2004/071558 | 8/2004 |
| WO | WO 2004/073554 | 9/2004 |
| WO | WO 2005/000680 | 1/2005 |
| WO | WO 2005/092000 | 10/2005 |
| WO | WO 2005/118033 | 12/2005 |
| WO | WO 2005/120607 | 12/2005 |
| WO | WO 2006/009839 | 1/2006 |
| WO | WO 2006/047087 | 5/2006 |
| WO | WO 2006/073394 | 7/2006 |
| WO | WO 2006/088513 | 8/2006 |
| WO | WO 2006/088630 | 8/2006 |
| WO | WO 2007/089727 | 8/2007 |
| WO | WO 2008/032291 | 3/2008 |
| WO | WO 2008/045161 | 4/2008 |
| WO | WO 2008/088609 | 7/2008 |
| WO | WO 2008/103997 | 8/2008 |
| WO | WO 2008/135719 | 11/2008 |
| WO | WO 2009/070603 | 6/2009 |
| WO | WO 2009/070605 | 6/2009 |

OTHER PUBLICATIONS

Yu Xinglong et al.: "Particle Acceleration for Delivery Deoxyribonucleic Acid Vaccine into Skin In Vivo", Review of Scientific Instruments, Aug. 2001, pp. 3390-3395, vol. 72, No. 8, American Institute of Physics.

* cited by examiner

NEEDLELESS SYRINGE

Matter enclosed in heavy brackets [ ] appears in the original patent but forms no part of this reissue specification; matter printed in italics indicates the additions made by reissue.

TECHNICAL FIELD

This invention relates to needleless syringes for use in delivering particles into target tissue of a subject, for example skin or mucosa. Said particles may, for example, comprise a drug, vaccine, diagnostic agent or carrier particle coated with a genetic material (or any combination thereof).

BACKGROUND OF THE INVENTION

The ability to deliver pharmaceuticals through skin surfaces (transdermal delivery) provides many advantages over oral or parenteral delivery techniques. In particular, transdermal delivery provides a safe, convenient and noninvasive alternative to traditional drug administration systems, conveniently avoiding the major problems associated with oral delivery (e.g. variable rates of absorption and metabolism, gastrointestinal irritation and/or bitter or unpleasant drug tastes) or parenteral delivery (e.g. needle pain, the risk of introducing infection to treated individuals, the risk of contamination or infection of health care workers caused by accidental needle-sticks and the disposal of used needles). In addition, transdermal delivery affords a high degree of control over blood concentrations of administered pharmaceuticals.

A novel transdermal drug delivery system that entails the use of a needleless syringe to fire powders (i.e. solid drug-containing particles) in controlled doses into and through intact skin has been described. In particular, U.S. Pat. No. 5,630,796 to Bellhouse et al. describes a needleless syringe that delivers pharmaceutical particles entrained in a supersonic gas flow. The needleless syringe is used for transdermal delivery of powdered drug compounds and compositions, for delivery of genetic material into living cells (e.g. gene therapy) and for the delivery of biopharmaceuticals to skin, muscle, blood or lymph. The needleless syringe can also be used in conjunction with surgery to deliver drugs and biologics to organ surfaces, solid tumours and/or to surgical cavities (e.g. tumour beds or cavities after tumour resection). In theory, practically any pharmaceutical agent that can be prepared in a substantially solid, particulate form can be safely and easily delivered using such devices.

One needleless syringe described in U.S. Pat. No. 5,630,796 comprises an elongate tubular converging-diverging nozzle having a rupturable membrane initially closing the passage through the nozzle and arranged substantially adjacent to the upstream end of the nozzle. Particles of a therapeutic agent to be delivered are disposed adjacent to the rupturable membrane and are delivered using an energizing means which applies a gaseous pressure to the upstream side of the membrane sufficient to burst the membrane and produce a supersonic gas flow (containing the pharmaceutical particles) through the nozzle for delivery from the downstream end thereof. The particles can thus be delivered from the needleless syringe at very high velocities which are readily obtainable upon the bursting of the rupturable membrane. The passage through the nozzle has an upstream convergent portion, leading through a throat to a downstream, divergent portion. The converging-diverging passage is used to accelerate the gas to supersonic speed. The gas is first brought to Mach 1 in the throat and the downstream divergence accelerates it to a steady state supersonic speed.

With the syringes described in U.S. Pat. No. 5,630,796 particles can be delivered at a large range of velocities with potentially non-uniform spatial distribution across the target surface. A variation in particle velocity can make it difficult to deliver high-potency powdered drugs, vaccines etc to specific target layers within the skin. Furthermore, non-uniform spatial distribution can cause problems which would be ameliorated if a more even spatial distribution could be achieved. In addition, flow considerations inside the syringes can limit the maximum size of the target area on the target tissue over which the particles may be spread, limiting the maximum particle payload size.

Additionally, with the syringes described in U.S. Pat. No. 5,630,796 the bursting of the rupturable membrane can make operation of the syringe fairly noisy, which can be a disadvantage when treating small children for example.

It would be advantageous to have a needless syringe which operates quietly and in which the particles may be spread over a larger target area, with a reasonably uniform distribution over that target area. By spreading the particles of the payload over a larger target area, with good uniformity of particle distribution over that target area, larger payloads may be delivered.

SUMMARY OF THE INVENTION

According to a first aspect of the present invention there is provided a method of distributing particles in a flow of gas from a needleless syringe, the method comprising:

(a) flowing gas through a first convergence in a gas flow path within the syringe thereby expanding the gas and reducing its pressure to provide a region of reduced gas pressure;

(b) utilizing said reduced gas pressure to draw a payload of particles into said gas flow path from outside of said gas flow path and to entrain them in the gas flow in said gas flow path; and (c) directing the gas through a delivery nozzle bounding said gas flow path so as to accelerate the entrained particles and cause the entrained particles to be distributed across substantially the full width of the nozzle at the nozzle's downstream exit.

By distributing the particles in the flow of gas from a needleless syringe using the method of the above first aspect of the present invention, whilst the nozzle's downstream exit is positioned adjacent a target area of skin or mucosa, the particles may be administered to the skin or mucosa.

According to a second aspect of the present invention there is provided a needleless syringe for use in the needleless injection of particles into the tissue of a vertebrate subject, the syringe comprising:

- a gas flow path arranged to receive gas from a gas source;
- a first convergence in said gas flow path for reducing the pressure of the gas flowing through said gas flow path;
- a particle inlet in communication with said gas flow path downstream of at least the start of said first convergence that allows a payload of particles to be drawn into the gas flow path via the inlet under the action of reduced pressure gas to become entrained in the gas; and
- a gas/particle exit nozzle bounding said gas flow path for the acceleration therealong of the drawn in particles entrained in the gas.

The use of a reduced pressure to draw particles into the gas flow path allows the membranes which were previously used to retain the particles to be dispensed with. This in turn ensures that the device works more quietly since the noise created by the bursting of the membrane is no longer present.

Preferably, the device is so constructed and arranged that substantial boundary layer separation between the wall of the nozzle and the gas jet is avoided thus enabling the particles accelerated out of the exit nozzle in the gas jet to be distributed across substantially the full width of the nozzle's downstream exit.

By avoiding substantial boundary layer separation of the gas jet from the nozzle wall, the particles being accelerated can be distributed across substantially the full cross-section of the nozzle at the nozzle's downstream exit. Where the nozzle has a divergent downstream section, it has been found that by extending the length of the nozzle to increase the diameter of the nozzle at its downstream exit, significantly larger target areas on the skin or mucosa may be penetrated by the particles, with good uniformity of distribution across the larger target area.

According to a third aspect of the present invention there is provided a method of creating a gas flow in a needleless syringe, said method comprising:

flowing gas through a first convergence into a chamber of increased cross-section to form a transsonic gas jet in said chamber;

passing the gas jet from the chamber through a second convergence into and along a nozzle.

The use of two convergences in this manner has been found to be a particularly advantageous way of creating a gas flow field suitable for accelerating particles in a needleless syringe.

BRIEF DESCRIPTION OF THE FIGURES

Embodiments of apparatus in accordance with the present invention will now be described, by way of example only, with reference to the accompanying drawings, in which.

DETAILED DESCRIPTION OF PREFERRED EMBODIMENTS

Figure 1:
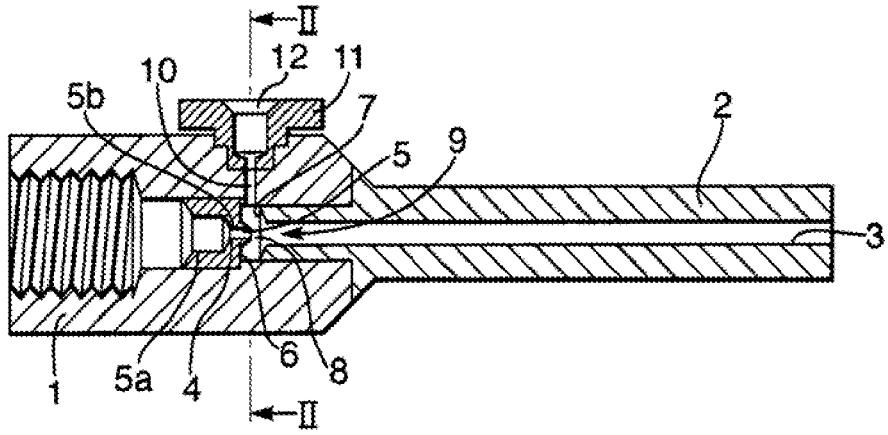
FIG. 1 is a schematic cross-section along the central longitudinal axis of the downstream end of a first embodiment of a needleless syringe.

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an" and "the" include plural referents unless the context clearly dictates otherwise. Thus, for example, reference to "a therapeutic agent" includes a mixture of two or more such agents, reference to "a gas" includes mixtures of two or more gases, and the like.

Definitions

Unless defined otherwise, all technical and scientific terms used herein have the same meaning as commonly understood by one of ordinary skill in the art to which the invention pertains.

The following terms are intended to be defined as indicated below.

The term "needleless syringe," as used herein, expressly refers to a particle delivery system that can be used to deliver particles into and/or across tissue, wherein the particles may have an average size ranging from about 0.1 to 250 μm, preferably about 1-70 μm, more preferably 10-70 μm. Particles larger than about 250 μm can also be delivered from these devices, with the upper limitation being the point at which the size of the particles would cause untoward pain and/or damage to the target tissue. The particles may be delivered at high velocity, for example at velocities of at least about 150 m/s or more, and more typically at velocities of about 250-300 m/s or greater. Such needleless syringes were first described in commonly-owned U.S. Pat. No. 5,630,796 to Bellhouse et al., incorporated herein by reference, and have since been described in commonly owned International Publication Nos. WO 96/04947, WO 96/12513, and WO 96/20022, all of which publications are also incorporated herein by reference. These devices can be used in the transdermal delivery of a therapeutic agent into target skin or mucosal tissue, either in vitro or in vivo (in situ); or the devices can be used in the transdermal delivery of generally inert particles for the purpose of non- or minimally invasive sampling of an analyte from a biological system. Since the term only relates to devices which are suitable for delivery of particulate materials, devices such as liquid-jet injectors are expressly excluded from the definition of a "needleless syringe."

The term "transdermal" delivery captures intradermal, transdermal (or "percutaneous") and transmucosal administration, i.e., delivery by passage of a therapeutic agent into and/or through skin or mucosal tissue. See, e.g., Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Aspects of the invention which are described herein in the context of "transdermal" delivery, unless otherwise specified, are meant to apply to intradermal, transdermal and transmucosal delivery. That is, the present invention, unless explicitly stated otherwise, should be presumed to be equally applicable to intradermal, transdermal and transmucosal modes of delivery.

As used herein, the terms "therapeutic agent" and/or "particles of a therapeutic agent" intend any compound or composition of matter which, when administered to an organism (human or animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, biological response modifiers, nucleic acids, gene constructs and the like. More particularly, the term "therapeutic agent" includes compounds or compositions for use in all of the major therapeutic areas including, but not limited to, adjuvants, anti-infectives such as antibiotics and antiviral agents; analgesics and analgesic combinations; local and general anesthetics; anorexics; antiarthritics; antiasthmatic agents; anticonvulsants; antidepressants; antigens, antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

The term "analyte" is used herein in its broadest sense to denote any specific substance or component that one desires to detect and/or measure in a physical, chemical, biochemical, electrochemical, photochemical, spectrophotometric, polarimetric, colorimetric, or radiometric analysis. A detectable signal can be obtained, either directly or indirectly, from such a material. In some applications, the analyte is a physiological analyte of interest (e.g., a physiologically active material), for example glucose, or a chemical that has a physiological action, for example a drug or pharmacological agent.

As used herein, the term "sampling" means extraction of a substance, typically an analyte, from any biological system across a membrane, generally across skin or tissue.

First Embodiment

FIG. 1 is a schematic cross-section along the central longitudinal axis of the downstream end of a first embodiment of needless syringe in accordance with the present invention. For reasons of clarity the gas source has been omitted. A possible gas source arrangement will be described later in conjunction with FIGS. 3, 16 and 19-22.

In FIG. 1 the main body 1 of the syringe has a central aperture extending therethrough to form a lumen which bounds the gas flow path through the syringe, into the downstream end of which is fitted a nozzle 2. As can be seen, the bore 3 of the nozzle is substantially parallel-sided, apart from a short taper at its upstream end.

Fitted generally midway along the central aperture of the main body 1 is a sonic nozzle 4. This sonic nozzle 4 is provided with an aperture which forms a first convergence or constriction 5 to the flow of gas through the main body 1. In this embodiment, the first convergence takes the form of two successive fairly abrupt constrictions 5a, 5b. The aperture of the first convergence is coaxial with the central longitudinal axis of the bore 3 of the nozzle 2.

The portion of the sonic nozzle 4 forming the downstream end of the constriction 5b projects outwardly (in a downstream direction) from the flat main downstream face 6 of the sonic nozzle 4. Although not shown, the sonic nozzle 4 may be held in place within the central aperture of the main body 1 by cooperating screwthreads, or an interference fit in combination with a downstream shoulder formed by the main body 1.

It will be noted that the flat, main downstream face 6 of the sonic nozzle 4 is spaced upstream from the upstream face 7 of nozzle 2. The two faces 6, 7, in combination with the central aperture of the main body 1 between those two faces 6, 7, define a chamber 8 for particle entrainment.

The upstream end of the nozzle 2 forms a second convergence or constriction 9 to the flow of gas through the main body 1. Again, in this embodiment, this convergence 9 is a fairly abrupt constriction. The nozzle 2 bounds the gas flow path, that is to say it surrounds and defines the space through which the gas may flow.

The sonic nozzle constriction 5b has a significantly reduced flow cross-section relative to the flow cross-section of the particle entrainment chamber 8. Similarly, the second convergence 9 has a much reduced flow cross-section relative to the flow cross-section of the chamber 8. In the illustrated embodiment, the nozzle 2 is 50 mm in length, the diameter of the sonic nozzle constriction 5b is 1 mm and the diameter of the exit nozzle constriction 9 is 2.3 mm. In contrast, the diameter of the particle entrainment chamber 8 is 5 mm. Consequently, the flow cross-section of the second convergence 9 is approximately 5.3 times larger than the flow cross-section of the first convergence 5. The ratio of flow cross-sections between the first and second convergences 5, 9 is relevant to the functioning of the syringe.

A particle inlet in the form of a particle inlet passage 10 is provided extending radially through the main body 1. The radially innermost end of the particle inlet passage 10 opens into the particle entrainment chamber 8 and the radially outer end of the passage 10 is arranged to communicate with a particle source 11 containing a payload of particles.

As can be seen from FIG. 1, the downstream tip of the sonic nozzle 4 defining the first convergence 5 (in turn comprising constrictions 5a and 5b), is generally coincident with the central longitudinal axis of the particle inlet passage 10. It is thought that this relative positioning is relevant if, as is described below, particles are to be drawn into the particle entrainment chamber 8 as a result of the creation of a reduced (sub-atmospheric in this embodiment) pressure region within the chamber 8. If the particle inlet passage 10 is in communication with a portion of the particle entrainment chamber 8 that is at atmospheric pressure or higher, particles will not be drawn into the particle entrainment chamber 8 when the syringe is fired, assuming the particle source is at atmospheric pressure.

In the embodiment illustrated in FIG. 1, the particle source 11 takes the form of a removable cassette having a central reservoir 12 in which the payload of particles (not shown) is deposited. When the cassette is engaged in a recess provided in the exterior side wall of the main body 1, for example to form an interference fit therewith, a hole in the cassette provided at the base of the reservoir 12 lines up in communication with the particle inlet passage 10. The top of the reservoir 12 is open to atmosphere.

Figure 2:
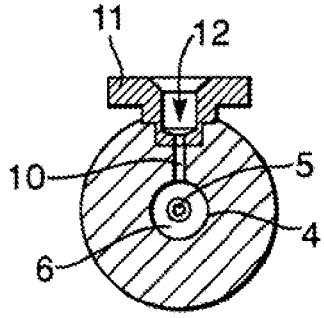
FIG. 2 is an axial cross-section taken along the line II-II in FIG. 1.
Figure 3:
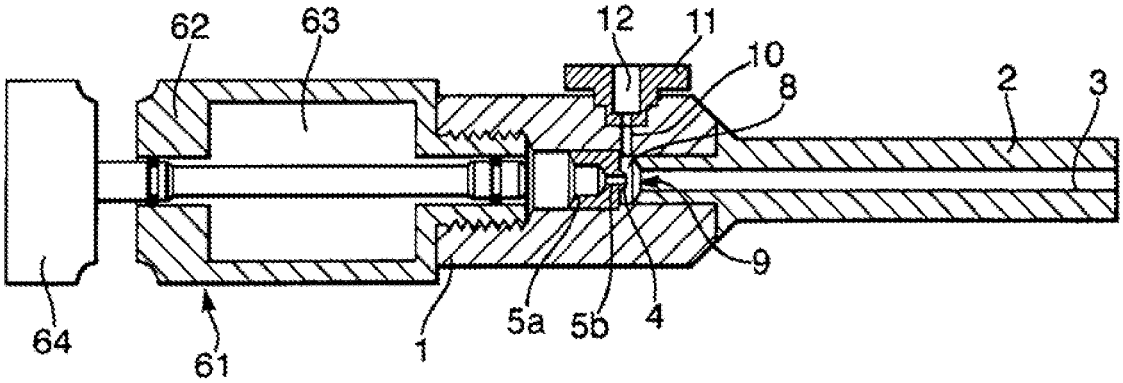
FIG. 3 is a schematic cross-section along the central longitudinal axis of a needleless syringe of the first embodiment of the invention, showing a push-button gas cylinder.

In order to operate the syringe illustrated in FIGS. 1 and 2, a gas source is necessary to pressurize the central aperture of the main body 1 upstream of the sonic nozzle 4 (ie. to the left of the sonic nozzle 4 as drawn in FIG. 1). This gas source may take the form of a gas canister linked to a button cylinder (not shown), with operation of the button cylinder releasing a fixed amount of gas (for example 5 ml), enabling the gas source to be used to deliver sequentially a plurality of discrete payloads of particles without needing to be recharged. Alternatively, a closed gas cylinder containing a single dose of gas sufficient for a single needleless injection may be provided. This last arrangement is preferred as will be discussed below. The preferred gas for the gas source is helium, with the gas cylinder containing helium gas at a pressure of between 15 and 35 bar, preferably around 30 bar. The preferred driver gas is helium because it gives much higher gas velocity than air, nitrogen or $CO_2$. The use of $CO_2$ as a source of driver gas is, however, superficially very attractive. Because, however, of the large variation of the saturation pressure of $CO_2$ with temperature, and the much lower velocities achievable therewith, the use of $CO_2$ may be limited. A single-shot button canister 61 comprising a plunger 64 and a sleeve body 62 defining a gas reservoir space 63 is shown attached to the FIG. 1 syringe in FIG. 3.

In use, in order to operate the needleless syringe, a known volume of gas at a known pressure is suddenly released from the gas source (not shown) into the central aperture of the main body to the upstream side of the sonic nozzle 4. The initial pressure is sufficiently high so as to establish choked flow of the gas at the exit of the sonic nozzle 4, at its smallest constriction 5b. The transsonic gas jet which issues from the constriction 5b into the particle entrainment chamber 8 expands to create a reduced pressure region in the particle entrainment chamber 8, in a manner similar to the venturi effect. The reduced pressure region is sub-atmospheric in this embodiment. It is this sub-atmospheric pressure region in cooperation with the atmospheric pressure in the particle source 11, which draws a payload of particles from the reservoir 12 of the particle source 11 into the chamber 8, along the particle inlet passage 10, and in so doing causes the drawn-in particles to become mixed and entrained in the expanding gas jet in the particle entrainment chamber 8.

As with all embodiments, helium is preferably used as the driver gas. However, the gas issuing from the device is actually a mixture of helium and air, due to the air that is drawn in along with the particles via the particle inlet passage 10. Typically, the gas comprises about 15% air (by mass) at exit (the rest being helium).

The relative sizes of the first and second convergences 5,9, as well as the longitudinal spacing therebetween, is such as to encourage the expanding, diverging gas jet to attach to the walls of the second convergence 9 and to remain attached to the walls of the nozzle 2 as the jet passes down the bore 3 of the nozzle 2. The radius of the chamber 8 is not thought to be particularly important although it should be large enough so that a free jet is capable of being formed in the chamber. By remaining attached, and thus avoiding substantial boundary layer separation of the gas jet from the walls of the second convergence 9 and the nozzle bore 3, the particles entrained in the gas jet are distributed across substantially the full cross-section of the nozzle bore 3. In this way, when the gas jet, with particles entrained therein, exits the nozzle's downstream exit and impacts a target area of tissue (eg. skin or mucosa) positioned in close proximity to the nozzle exit, the size of the target area impacted by the particles will be generally equal to the size of the bore 3 at the downstream exit of the nozzle 2 and the particles will be well distributed across the target area. By avoiding the formation of a substantial concentration of the particles within the core of the target area with no or few particles around the boundary of the target area, increased payloads of particles may be delivered without the central core of the target area becoming overloaded with particles.

Example of Performance of First Embodiment

When a syringe similar to that illustrated in FIGS. 1 and 2 was operated with a 5 ml button cylinder, (shown in FIG. 3) filled with air at a pressure of approximately 30 bar, and using a 1.0 to 1.5 mg payload of 55 μm lidocaine powder, the syringe was able to deliver the payload in such a way as to consistently anaesthetise a 2 to 3 mm diameter of the forearm within one minute. Given that the diameter of the nozzle bore 3 at the exit was 2.3 mm, the good spread of the particles across a target area substantially equal to the area of the nozzle bore 3 at the nozzle exit 2 will be appreciated.

Comparable performance was achieved with a canister containing helium at a pressure of 20 bar. When used with the 2.3 mm nozzle bore exit diameter syringe illustrated in FIGS. 1 and 2, satisfactory anaesthesia was obtained. Helium driver gas is in any event preferred to air as it gives more consistent behavior.

Performance comparisons (of which more later) between the different embodiments were made by discharging the embodiment of device, loaded with a known payload (between 1 mg and 3 mg) of 48 μm diameter polystyrene spheres above a 3% agar gel target. Vented spacers were fitted to the end of the device nozzle so as to keep the devices at a fixed distance from the target surface and at right angles to it. After firing off the syringe the agar was then photographed to record the delivery footprint. The gel target was then sliced across its diameter and thin sections were photographed through a microscope to establish the depth of penetration of the individual particles.

Figure 4:
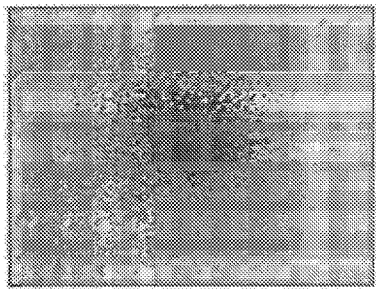
FIG. 4 is a top plan view of the target area of a gel target after the firing at it of particles from the first embodiment of syringe.
Figure 5:
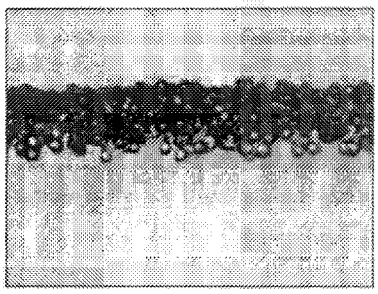
FIG. 5 is an enlarged cross-section through the gel target of FIG. 4, showing particle distribution across and penetration into the target.

FIGS. 4 and 5 show the footprint and penetration near the center of the target of polystyrene spheres delivered from the first embodiment of device, at the conditions found to provide anaesthesia with lidocaine (ie. 3 ml cylinder filled with helium to 20 bar). The footprint diameter was 3 mm and the maximum depth of particle penetration was about 180 μm.

Second Embodiment

Although the anaesthetic performance of the FIGS. 1 and 2 device was rapid and effective, because of the generally parallel-sided nature of the bore 3 in the nozzle 2 the target area on the target tissue was still fairly small (of the order of 3 mm diameter).

Figure 6:
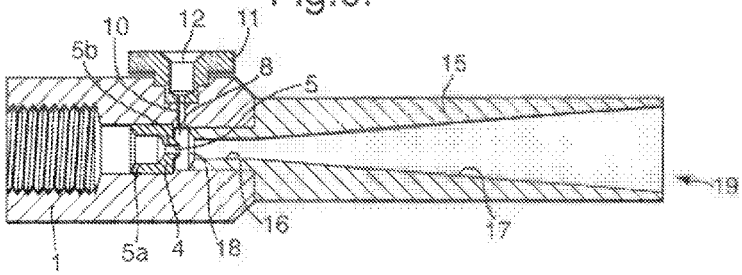
FIG. 6 is a schematic cross-section along the central longitudinal axis of the downstream end of a second embodiment of a needleless syringe.

FIG. 6 shows a second embodiment of a syringe in which the nozzle, instead of having a substantially parallel-sided bore, has a distinct divergence. In FIG. 6, components similar to components in FIGS. 1 and 2 have been given the same reference numerals. The reference numerals associated with the nozzle have, however, been changed.

In the FIG. 6 arrangement, the nozzle 15 comprises a short, upstream, parallel-sided section 16, leading into a long, divergent, downstream section 17. In the FIG. 6 embodiment, the diameter of the upstream parallel-sided section 16 is 2.3 mm. This section 16 forms the second convergence or constriction 18 to gas flow. In the FIG. 6 embodiment, the diameter of the minimum area of the first convergence or constriction 5 is 1.0 mm, such that the area of the flow cross-section of the second convergence 18 is approximately 5.3 times the area of the flow cross-section of the first convergence 5.

The length of the upstream parallel-sided section 16 of the bore of the nozzle 15 is 7 mm. After the upstream parallel-sided section 16, the divergent downstream section 17 has a cone angle of approximately 8.8° and diverges to provide the bore of the nozzle 15 with a 10 mm exit diameter at the nozzle's downstream exit 19.

The divergent section 17 is thought to allow the jet issuing from the sonic nozzle 4 to continue to expand supersonically before being broken down by a series of oblique shocks.

Example of Performance of Second Embodiment

Figure 7:
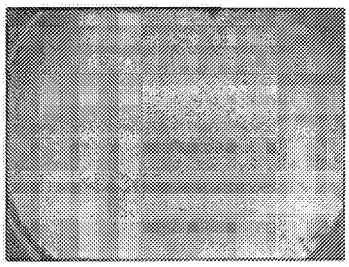
FIG. 7 is a top plan view of the target area of a gel target after the firing at it of a 1 mg payload of particles from the second embodiment of a syringe.
Figure 8:
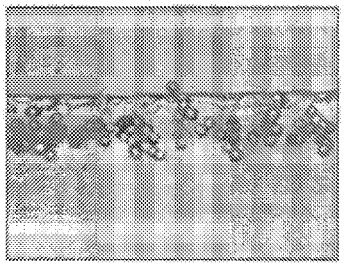
FIG. 8 is an enlarged cross-section through part of the gel target of FIG. 7, showing particle distribution across and penetration into the target.
Figure 9:
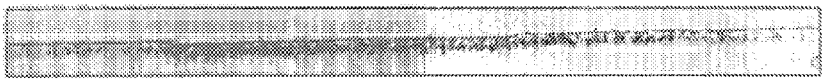
FIG. 9 is an enlarged cross-section through the full diametral width of the gel target of FIG. 7.

When the syringe of FIG. 6 was fired, with the gas source as a 5 ml cylinder filled with helium at 25 bar, a 1 mg payload of lidocaine powder was successfully distributed over a target area having a diameter of just over 10 mm, approximately equal to the diameter of the nozzle's downstream exit 19. The maximum particle penetration was found to be about 180 μm. Once again, the particle distribution over the target area was highly uniform. FIG. 7 is top plan view of the agar target. FIG. 8 is a magnified cross-section of a diametral slice through the agar target, showing the penetration of the individual particles. FIG. 9 is a reconstruction of a diametral 10 mm wide slice through the agar target, showing the uniformity of distribution and penetration of the particles across the full width of the target.

As with the first embodiment, with the second embodiment it is thought that the good distribution of particles across a target area substantially equal to the size of the nozzle at the nozzle's downstream exit is influenced by the relative minimum sizes of the first and second convergences 5, 16, the distance by which they are spaced apart and the positioning of the particle inlet passage 10 relative to the exit of the first convergence and the entrance to the second convergence. In the second embodiment, it is thought also to be advantageous to have an upstream parallel-sided section 16 ahead of the divergent downstream section 17, as it is thought that the parallel-sided section 16 assists in settling down the gas flow and reattaching to the nozzle walls the diverging gas jet emanating from the first convergence 5.

Clinical Trial Results

A small scale clinical trial was conducted with the first and second embodiments of the syringe to test their efficacy when delivering lidocaine to the human skin.

Five volunteers had 1.5 mg of lidocaine administered to their volar forearms. After three minutes, two needle probes were used to compare the pain experienced at the treated site with that at an untreated site close by. All but one of the volunteers found that the needle probes at the active sites were less painful than those at the non-active sites. Subsequently two volunteers tested lidocaine administrations to the fossa. Both found that the treated sites were completely pain free.

Figure 10:
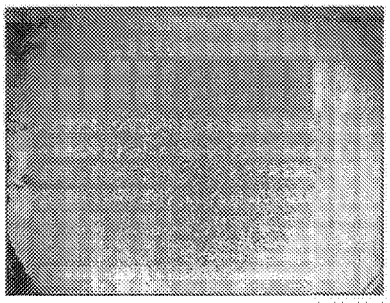
FIG. 10 is a top plan view of the target area of a gel target after the firing at it of a 2 mg payload of particles from the second embodiment of the syringe.
Figure 11:
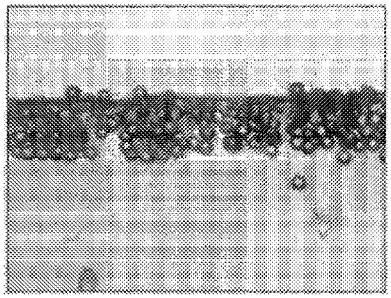
FIG. 11 is an enlarged cross-section through part of the gel target of FIG. 10.

The first embodiment of syringe appeared to be more effective over a small area of forearm than the second embodiment of syringe used with the same particle payload. Because, however, the particle penetration depth was similar in both cases a likely explanation for this is that insufficient lidocaine particles were being administered to the 10 mm diameter target area with the second embodiment of syringe. FIGS. 10 and 11 show the effect of doubling the payload from 1 mg to 2 mg in the second embodiment. The penetration depth is slightly reduced to 160 μm (from 180 μm), but the particles are more densely packed.

Figure 12:
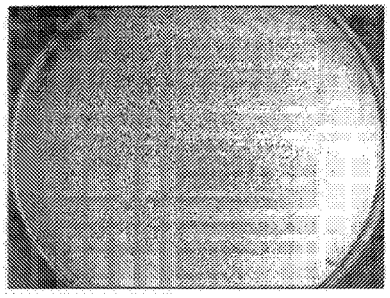
FIG. 12 is a top plan view of the target area of a gel target after the firing at it of a 3 mg payload of particles from the second embodiment of the syringe.
Figure 13:
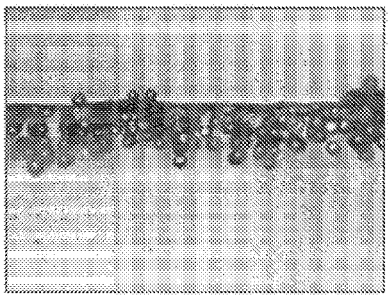
FIG. 13 is an enlarged cross-section through part of the gel target of FIG. 12.

The second embodiment of syringe was also modified by extending its nozzle 15 in length. By maintaining the same taper angle of 8.8 degrees, the diameter of the nozzle at its downstream exit 19 was increased to 14 mm from 10 mm. This modified arrangement was tested with a 3 mg payload of lidacaine powder using a 5 ml cylinder of helium at 30 bar. The results are shown in FIGS. 12 and 13. Although penetration depth has again fallen slightly (to 140 μm), the powder was still found to be substantially uniformly distributed over the full target area, the target area of course this time having a diameter of approximately 14 mm.

Third Embodiment

Figure 14:
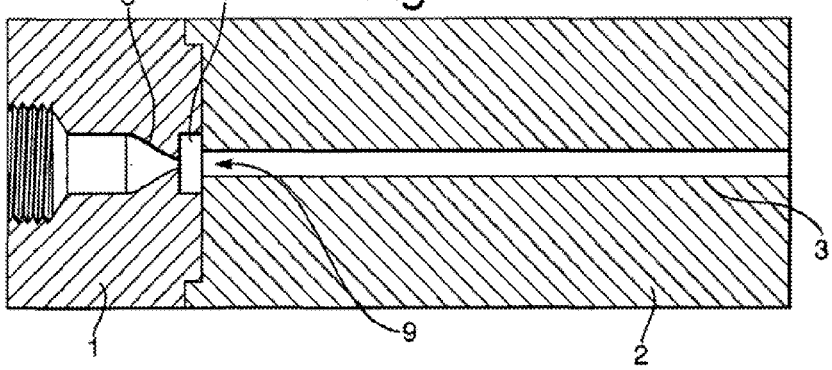
FIG. 14 is a schematic cross-section along the central longitudinal axis of a needleless syringe according to a third embodiment of the present invention, showing an alternative geometry of first convergence.

The first and second embodiments described above utilize a first convergence or constriction 5 to create a reduced pressure region which is used to draw in a payload of particles. The first convergence or constriction as described comprises an upstream constriction 5a and a downstream constriction 5b. It is the smaller downstream constriction 5b that is choked during use. The third embodiment relates to a modification of this geometry which replaces the two-stage convergence of the first and second embodiments with a smoothly tapering convergence 5'. As shown in FIG. 14, the convergence 5' tapers down from a diameter of 6 mm at the upstream end to a diameter of 1.2 mm at the downstream end over a length of about 17 mm. As with the first and second embodiments, high pressure gas presented to the upstream end of the convergence will tend to have its pressure reduced as it flows along the gas flow path through the convergence 5' and into the chamber 8. This reduced pressure can then be used to draw in a payload of particles from the particle source 11 (not shown in FIG. 14).

The chamber 8 is the preferred position for the particle inlet passage 10 (not shown in FIG. 14) and it has been found that the transsonic gas jet formed effectively entrains the particles such that they are uniformly distributed in the gas flow. However, it is not essential that the particles are introduced in this chamber and in fact they may be introduced at any position in the device where there is a reduced pressure region in the gas flow path. Since the reduced pressure stems from the Venturi effect caused by the first convergence 5', the device is still effective when the particles are introduced upstream of the chamber 8, in the first convergence 5'. It is enough that the gas flow path has started to converge at the position where the particle inlet passage 10 is located such that there is a reduction in pressure sufficient to draw in the particles. Similarly, the particle inlet passage 10 may be located downstream of the chamber 8 either at the second convergence 9 or downstream thereof in the nozzle bore 3. It has been found that the gas pressure in these positions is reduced to a value sufficient to cause the drawing in effect of the particles.

The third embodiment works in a very similar way to the first and second embodiments in so far as there is provided a first convergence or constriction followed by a chamber of increased cross-section followed by another convergence or constriction. The chamber of increased cross-section is thought to provide a discontinuity to the gas flow which leads to the creation within the chamber of a transsonic jet, which jet passes through the chamber and attaches to the walls of the nozzle bore 3 in the region of the second convergence 9. As the transsonic jet enters the second convergence, a normal shock wave is thought to be formed across the second convergence which increases the pressure and reduces the velocity of the gas. The nozzle portion then serves to accelerate the particles in the already quickly moving gas stream.

As already mentioned, the first and third embodiments (with a parallel sided nozzle bore 3) are thought to have particular application in dentistry where it is useful to achieve penetration of a small target area and where the mucosal surfaces are relatively easy to penetrate. This in turn means that low driving pressures can be used (i.e. the pressure presented to the first convergence 5), such as 10 bar for example. It has been found that the lower the driving pressure, the less noise that is created by the device.

In all embodiments, the mass flow rate of gas through the device is determined by the driver pressure and the smallest cross sectional flow area in the device. This smallest area is preferably the first convergence 5, 5'. Thus, it is expected that the first convergence will be choked during normal operation.

Fourth Embodiment

Figure 15:
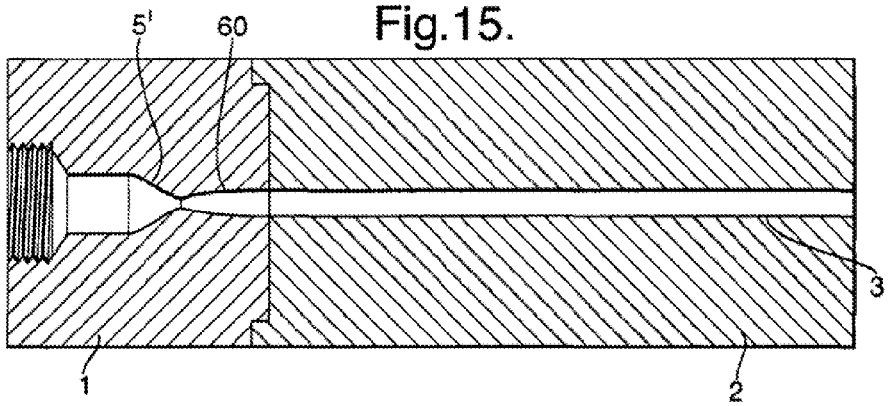
FIG. 15 is a schematic cross-section along the central longitudinal axis of a needleless syringe according to a fourth embodiment of the present invention showing a divergent section instead of a particle entrainment chamber.

FIG. 15 shows a fourth embodiment of needleless syringe in accordance with the present invention in which the chamber 8 has been replaced by a divergent section 60. The first convergence or constriction 5' is shown as having a tapered form similar to that in FIG. 14, although the two-stage first convergence 5a, 5b of the embodiments of FIGS. 1 and 2 would also be acceptable. In this embodiment, because there is no chamber 8, there is no second convergence as such and the gas flow path diverges from the point of minimum cross-section of the first convergence 5' to the cross-section of the nozzle bore 3. This change in geometry means that no trans-sonic jet is formed and instead the configuration acts like a convergent-divergent nozzle which accelerates the flow to supersonic speeds (with low static pressures). The particle payload can be introduced at any point in the gas flow where the pressure is low enough to cause the drawing-in effect to take place. In practice this is a position between a point in the convergence 5' where the pressure has reduced enough to a point in the nozzle bore 3 far enough upstream to give the particles adequate residence time in the nozzle to achieve the desired velocity. Thus, the particle inlet passage 10 may be positioned anywhere in the divergent section 60.

Fifth Embodiment

Figure 16:
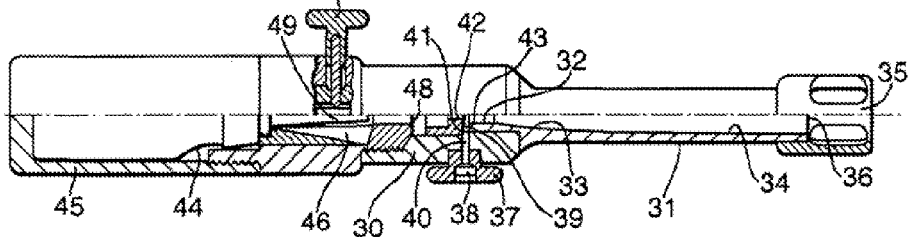
FIG. 16 is a cross-section along the central longitudinal axis of a fifth embodiment of a needleless syringe.

In FIGS. 1-2 and 6 the gas source is not shown. As mentioned above, the gas source may advantageously take the form of a single shot gas canister, preferably a helium gas canister. To show one possible arrangement for this gas canister, FIG. 16 shows a fifth embodiment of a syringe in accordance with the present invention. In this fifth embodiment, the main body 30 is provided with a nozzle 31 having an upstream parallel-sided section 32, a short divergent section 33 downstream thereof, followed by a long downstream generally conical section 34. Provided on the downstream end of the nozzle 31 is a spacer 35, whose downstream face is intended to be placed against the skin or mucosa surrounding the target area to space the nozzle's downstream exit face 36 from the target area. As can be seen the spacer 35 is provided with a plurality of radial outlets to allow the escape of the driver gas.

As in the first to fourth embodiments, the particle source 37 takes the form of a cassette having a reservoir 38 provided therein to receive the payload of particles. This reservoir 38 is in communication with the particle entrainment chamber 39 via the particle inlet passage 40.

Provided at the upstream end of the particle entrainment chamber 39 is a sonic nozzle 41, whose central aperture forms the first convergence or constriction 42 to the flow of gas from the gas source. The second convergence or constriction 43 is provided by the upstream end of the upstream parallel-sided section 32 of the bore of the nozzle 31. The minimum diameters of the first and second convergences shown are 1 mm and 2.3 mm respectively.

The gas source is positioned to the left (as drawn) of the main body 30. The gas source includes a gas cylinder 44 received within a housing 45. The right-hand end (as drawn) of the gas cylinder 44 is provided with a longitudinally extending nose 49, which nose is capable of being fractured, so as to allow the escape of gas from the interior of the cylinder 44, upon the application of lateral pressure to the nose 45 in the direction identified by the arrow referenced 46. In the illustrated embodiment, this lateral pressure is applied by moving a plunger 47 radially inwardly, using the pressure from a thumb or finger, sufficiently far as to fracture the nose 49 and to cause gas release from the cylinder 44. It is this release of gas which pressurizes the space upstream of the sonic nozzle 41, leading to choked flow of the released gas through the first convergence 42.

The gas cylinder 44 need not have its nose pointed to the right (as drawn). It may, for example, be turned through 180° so that its nose points to the left.

So as to avoid the possibility of any fragments from the fracturing of the nose either blocking the sonic nozzle 41, or passing through the aperture provided in the sonic nozzle 41, a thin gauze filter 48 may, as shown, be provided between the gas cylinder 44 and the sonic nozzle 41 so as to filter the gas from the cylinder prior to its passage through the sonic nozzle 41.

The method and mechanism of operation of the fifth embodiment is similar to that of the first to fourth embodiments and will not be further described here.

In all the embodiments, the relationship between the area of the first and second convergences (or the relationship between the area of the first convergence and the area of the nozzle in the fourth embodiment) is thought to be significant. Diameters of 1.0 and 2.3 mm for the first and second convergences respectively, equating to a flow cross-sectional area ratio of 1:5.3 worked well. Other constructions that worked well were diameters of 1.2 and 3.0 mm for the first and second convergences, 1.3 and 3 mm for the first and second convergences and 1.4 and 3.5 mm for the first and second convergences respectively, equating to flow cross-sectional area ratios of 1:6.25, 1:5.3 and 1:6.25 respectively. In contrast, diameters of 1.2 and 2.3 for the first and second convergences respectively, equating to a ratio of 1:3.7 did not work well.

For the larger diameter first convergence (e.g. 1.4 mm), a larger mass flow rate can be established and a more powerful device can be constructed. Pressures of up to 60 bar may be used as a driver, in order to provide enough propellent to support the increased mass flow rate.

In the illustrated embodiments, the particle source 11, whilst suitable for use in the laboratory, would not be particularly well suited to commercial use because the powder to be delivered could become contaminated and/or fall out of the reservoir provided in the particle source cassette.

Figure 17:
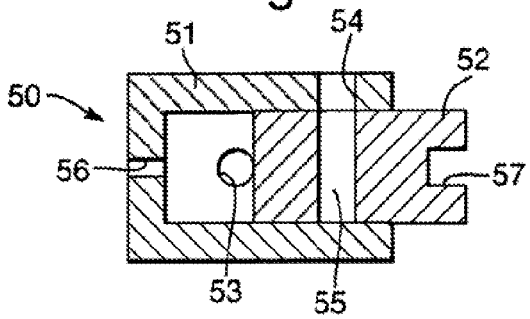
FIG. 17 is a schematic cross-section, on an enlarged scale, along the central longitudinal axis of a disposable drug cassette suitable for use with a needleless syringe.

FIG. 17 shows one possible way of sealing a metered quantity of powder in a sealed container until it is ready for use. In FIG. 17 the particle source 50 has a two-piece construction, comprising a cassette body 51 and a rotatable and axially slidable plug 52.

The cassette body 51 has three radial holes 53, 54 provided therein. Hole 54 is a single filling hole to enable the powder cavity 55 in the plug 52 to be filled with a metered dose of powder. A pair of diametrically opposed holes 53 are also provided, of which only one is visible in FIG. 12. One of these holes 53 is a powder exit hole. FIG. 14 shows the plug 52 in a position enabling the powder cavity 55 provided therein to be filled through the filling hole 54. After filling, the plug 52 is slid to the left (as drawn) to position the powder cavity 55 in the same plane as holes 53, but not to align it with either of holes 53. The cassette 50 can then be mounted on the syringe with one or other of its radial throughholes 53 aligned with the syringe's particle inlet passage leading to the particle entrainment chamber 8. To prime the cassette prior to use a tool, for example a screwdriver type blade, can be inserted into a slot 57 provided in the right-hand end (as drawn) of the plug, enabling the plug to be rotated through 90° within the cassette body 51 to bring the powder cavity 55 into alignment with both of the diametrically opposed holes 53. By priming the cassette in this way, when the syringe is then operated, air can enter through the upstream one of the pair of holes 53, enabling the powder in the cavity 55 to be carried out of the other of the pair of holes 53, through the particle inlet passage, into the particle entrainment chamber.

Figure 18A:
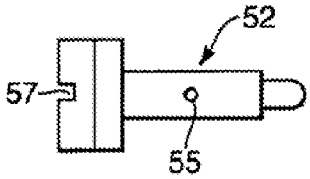
FIGS. 18a to 18f show views of a particle cassette and plug arrangement according to the present invention.
Figure 18B:
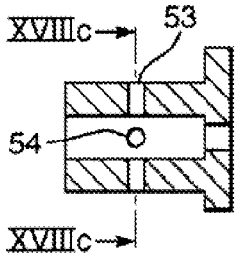
Figure 18C:
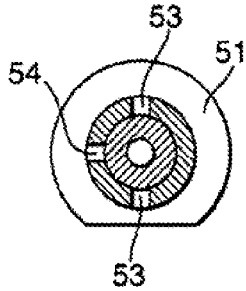
Figure 18D:
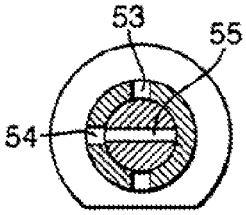
Figure 18E:
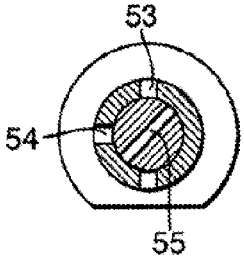
Figure 18F:
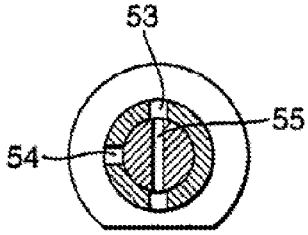

FIGS. 18a to 18f show a second way of sealing a metered quantity of powder in a sealed container until it is ready for use. The same reference numerals as FIG. 17 are used where possible. FIG. 18a shows a plug member 52, FIGS. 18b and 18c show orthogonal views of a cassette body 50 and FIGS. 18d to 18f show the plug member 52 inserted into the cassette body 50 in various orientations. As in FIG. 17, the cassette body 50 has three radial holes 53, 54 provided therein, a single filling hole 54, to enable the powder cavity 55 in the plug 52 to be filled with a metered dose of powder and a pair of diametrically opposed holes 53 which are used when the plug 52 is in the operating position (FIG. 18f). As with the FIG. 17 embodiment, the plug 52 is rotatable in the cassette body but, contrary to the FIG. 17 embodiment, is not meant to be actively slidable in use. Before filling, the plug 52 is aligned with filling hole 54 so that particles can be placed in the powder cavity 55 via hole 54 (see FIG. 18d). The plug 52 is then rotated (again by using a screwdriver in slot 57 or other means for turning, e.g. using a spanner or manually operating a lever built into the plug 52) by approximately 45° such that, although the powder cavity 55 is in the same plane as all three of the holes 53, 54, it is not in communication with any of them (see FIG. 18e). This storage position ensures that the powder cannot escape. In use, the plug 52 is rotated by a further 45° so that the particles come into fluid communication with each of the diametrically opposed holes 53 (see FIG. 18f). Thus, although similar to the FIG. 17 embodiment, this embodiment does not require the additional step of actively sliding the plug 52.

Figure 19:
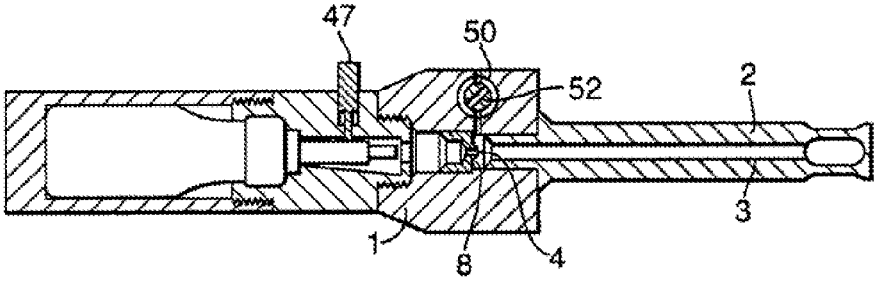
FIG. 19 is a schematic cross-section along the central longitudinal axis of a needleless syringe showing a particle cassette and gas cannister in place.

FIG. 19 shows the cassette body 50 and plug 52 mounted on a needleless syringe similar to that shown in FIG. 1. As can be seen, the cassette body 50 can be made integral with the syringe main body 1 so that the holes 53 are aligned with the particle inlet passage 10 and the atmosphere respectively.

It will be appreciated that there will be numerous other possible ways for hermetically sealing a pre-measured dose of powder prior to use of the syringe.

Exit Nozzle Configurations

Figure 20:
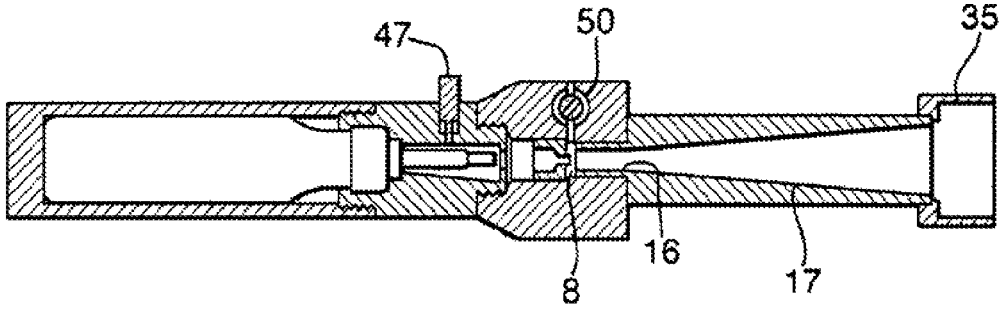
FIG. 20 is a view similar to FIG. 19, but with a different nozzle section that incorporates a divergence.

Various configurations of exit nozzle have been found to be effective. FIGS. 1 and 19 show an exit nozzle 2 having a substantially parallel sided bore 3. This can be used to deliver particles to a relatively small target area, and due to the localized delivery has been found to be particularly effective in dental applications for example in anesthesia. FIGS. 6 and 20 show an exit nozzle 2 having a relatively short parallel section 16 followed by a divergent section 17. This has been found to effectively increase the target area of particle penetration, although there seems to be a limit as to how much the exit nozzle can diverge before boundary layer separation takes place and the jet forms a "core" of particles which is smaller than the exit diameter of the nozzle.

Figure 21:
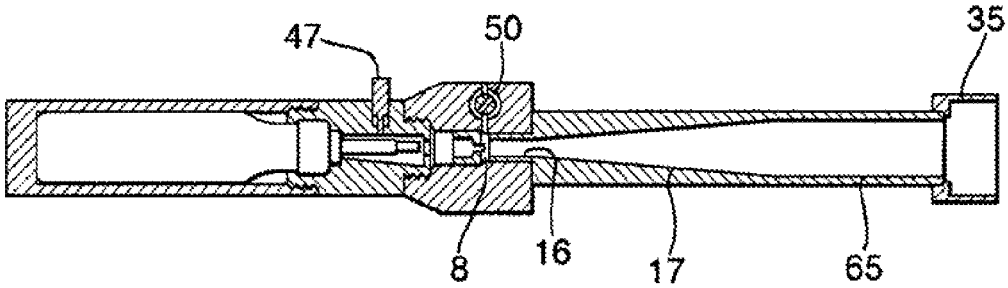
FIG. 21 is a view similar to that of FIGS. 19 and 20, except that the nozzle comprises a parallel sided extension section.

To address this problem of "coring", the nozzle shown in FIG. 21 has been developed in which a short parallel section 16 is followed by a divergent section 17 which in turn is followed by a parallel section 65. The downstream parallel section 65 following the divergent section 17 helps to reattach the boundary layer which can become separated in the divergent section 17 and yields a more uniform particle distribution across the whole exit diameter of the nozzle.

Sixth Embodiment

Figure 22:
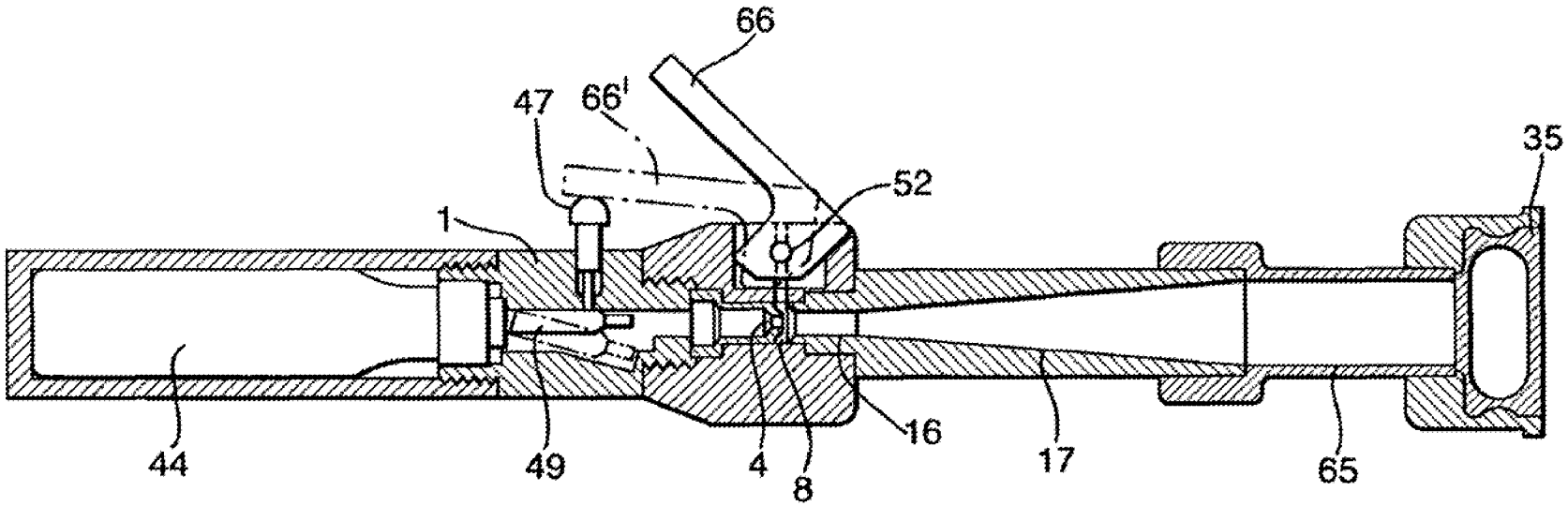
FIG. 22 is a schematic cross-section across the central longitudinal axis of a needleless syringe in accordance with a sixth embodiment of the present invention, showing a novel actuating lever.

FIG. 22 shows a sixth embodiment of the invention which combines many of The features of the previously described embodiments but also has a novel actuating Mechanism which serves to align the powder cassette plug 52 into the operating position and Actuates the cylinder fracturing mechanism in one simple operation. As can be seen from FIG. 22, an actuating lever 66 is provided which rotates about the same pivot axis (not shown) as the plug 52 of the powder cassette. Initially, the actuating lever 66 is provided in a primed position in which the powder cavity 55 is oriented at 45° from the position in which it is aligned with the particle inlet passage 10. This is the previously described "storage" position. The actuating lever 66 can be pressed by the thumb of an operator and in so doing rotates about its pivot axis to bring the powder cavity 55 almost into alignment with the diametrically opposed holes and thus bring the powder into fluid communication with the gas flow path (via the particle inlet passage 10). This position of actuating lever is also shown in FIG. 22 and is denoted by 66'. In the final stages of pressing the actuating lever 66, the lever 66 abuts the actuating pin 47 and further pressure causes the frangible tip 49 of the gas cylinder 44 to fracture and thereby triggers the device (FIG. 22 shows the frangible tip 49 in both an unbroken and broken position). The lever 66 typically turns 40° before it abuts the actuating pin 47 and the final 5° is used to fracture the cannister tip and bring the powder cavity 55 into full alignment. Thus, a mechanism is provided whereby the powder can be moved from the storage position to the operating position and the device can be triggered in one easy movement.

FIG. 22 is shown with the nozzle of FIG. 21 (parallel-divergent-parallel nozzle). However, any of the heretofore described nozzle designs maybe utilized, either with or without a spacer 35.

Seventh Embodiment

The above embodiments all utilize a first convergence 5, 5' to create a reduced pressure region which can be used to draw the particles into the gas flow path. In the embodiments shown, since the particles are initially provided in contact with the atmosphere, the reduced pressure must necessarily be sub-atmospheric for the effect to work properly. The seventh embodiment relates to a construction in which the particles are provided in fluid communication with an upstream portion of the gas flow path such that, in use, the reduced pressure need not be sub-atmospheric and need only be reduced compared to the pressure at that upstream portion of the flow path.

Figure 25:
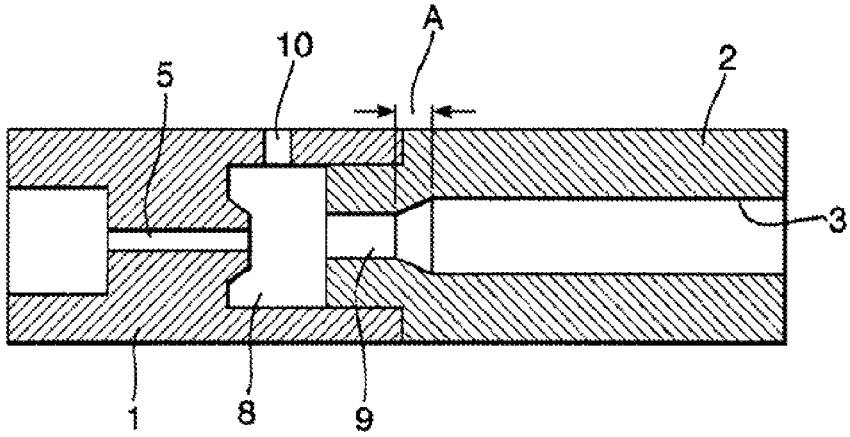
FIG. 25 is a schematic cross-section along the central longitudinal axis of the downstream end of a needleless syringe according to a ninth embodiment of the present invention, showing an alternative nozzle geometry referred to as a "fast expand" nozzle.
Figure 23:
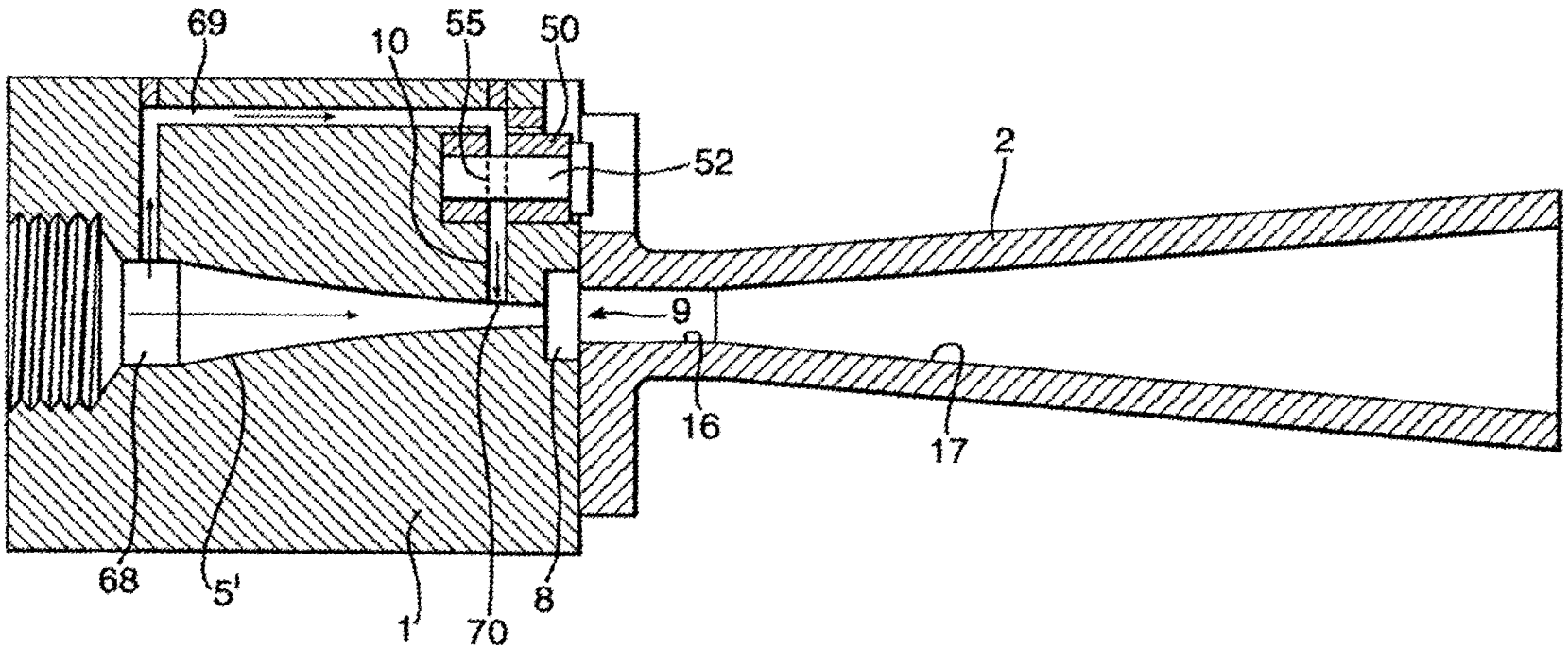
FIG. 23 is a schematic cross-section along the central longitudinal axis of the downstream end of a needleless syringe according to a seventh embodiment of the present invention, showing a configuration for injecting the particles into the flow stream.

FIG. 23 schematically illustrates the concept on a device having a similar construction to that shown in FIG. 14, but with a divergent nozzle. In FIG. 25, the powder cassette 50 is rotated 90° about a vertical axis as compared with the orientation shown in FIGS. 19 to 22, and the top hole 53 of the powder cassette 50, instead of being vented to atmosphere, is provided in fluid communication with an upstream part 68 of the gas flow path, upstream of the first convergence 5'. This fluid communication is achieved by passage 69. The particle inlet passage 10 fluidly communicates with the other hole 53 of the particle cassette 50 and a more downstream part 70 of the convergence 51. The convergence 5' causes a reduction in gas pressure, in use, due to the Venturi effect such that there is, in use, a pressure differential across the powder cavity 55. Thus, even if the pressure in the gas flow path at a position 70 adjacent the particle inlet passage 10 is not sub-atmospheric, the particles are still drawn into the gas flow path because the pressure is at least reduced compared to the pressure to which the particles are exposed (i.e. that pressure present at the upstream end 68 of the device).

The amount of gas which flows along the passage 69 is preferably small compared to the flow rate along the gas flow path, e.g. 20% or so.

Theoretically, gas pressure close to the driver pressure can be used to inject the particles into the gas flow. Typically, though, the particle inlet passage 10 and passage 69 are positioned so that about 0.2 times the driver pressure is present across the particles in use. When 30 bar driver pressure is used, this corresponds to a pressure difference of 6 bar which serves to draw the particles into the flow. By modifying this pressure difference, the time at which the particles are drawn into the flow can be controlled. This timing can also be controlled by modifying the length and/or tortuousness of the passage 69.

Thus, this embodiment provides a form of particle "injection" and gives greater flexibility as to where the particles can be introduced since the requirement for sub-atmospheric pressure is dispensed with. Although the particles are shown being injected into the first convergence 5', they may be injected into the chamber 8, the second convergence 9, the nozzle bore 3, 16, 17 or the divergent section 60 as described in relation to the other embodiments.

This embodiment has the further advantage that no atmospheric air is induced into the gas flow meaning that the device is self-contained in use. This reduces the possibility of contamination of the particles by contaminants suspended in atmospheric air.

Eighth Embodiment

As described above, a large divergent portion 17 of the exit nozzle 2 can cause "coring" whereby the boundary layer separates from the nozzle walls and the majority of the jet power is concentrated along a central longitudinal axis such that the particles are not evenly distributed across the full area of the nozzle at the nozzle exit plane. This can be ameliorated by the use of a second parallel section 65 (see FIG. 21) and it is thought the parallel section 65 encourages re-attachment of the boundary layer in the nozzle. However, it is desirable to prevent the initial detachment to provide a more desirable gas flow from the point of view of good particle injection. The eighth embodiment provides a further modification to the divergent section 17 of the exit nozzle which can ameliorate this effect.

Figure 24:
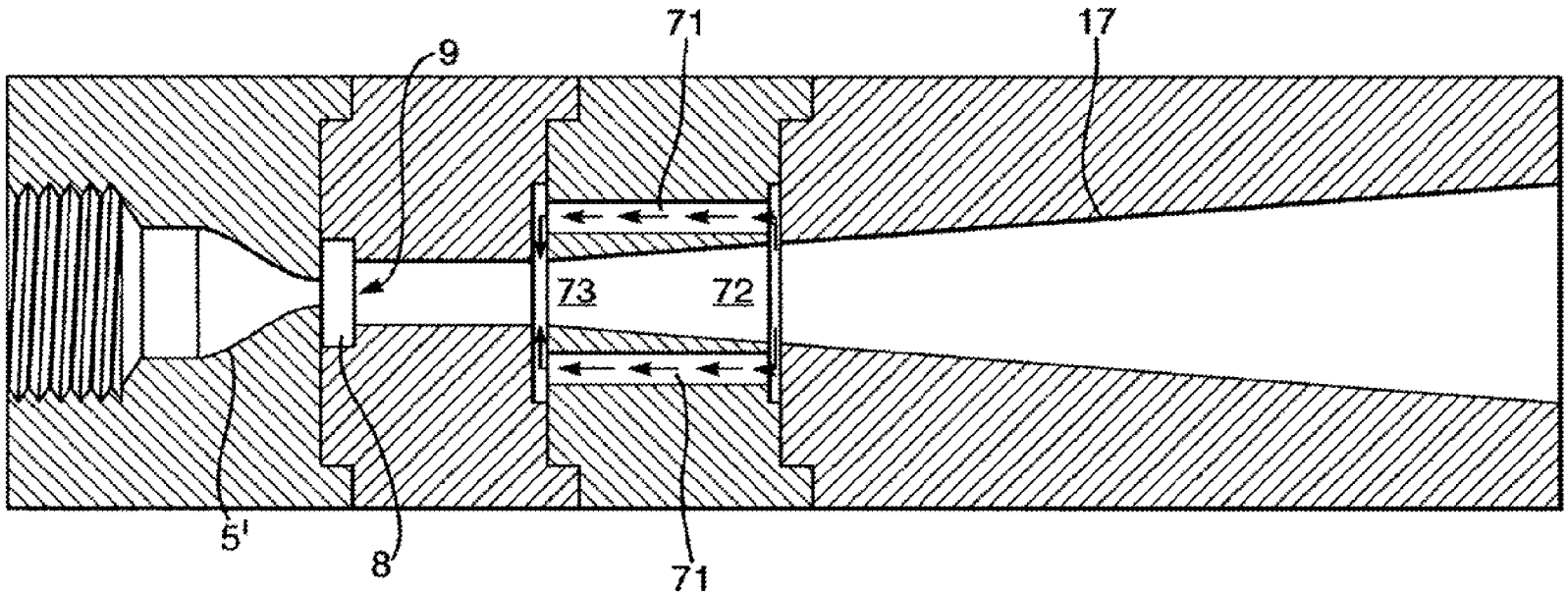
FIG. 24 is a schematic cross-section along the central longitudinal axis of the downstream end of a needleless syringe according to an eighth embodiment of the present invention, showing a configuration for preventing boundary layer separation of the jet.

FIG. 24 schematically shows the principle as applied to the embodiment of FIG. 14, but with a divergent nozzle. A return gas flow path 71 is provided between a point 72 in the divergent nozzle and a point 73 upstream of that point 72. The Venturi effect means that the position 73 of lower cross-sectional area will have a reduced pressure as compared to the position 72 of higher cross-sectional area. This will cause gas flow to be routed from the downstream point 72 to the upstream point 73 due to the pressure differential in use. This creates a suction effect near the walls of the nozzle at the downstream point 72 which tends to delay separation of the boundary layer from the walls. This embodiment can therefore be utilized to provide a more even spread of particles and less "coring" of the gas stream.

Ninth Embodiment

This embodiment utilizes a further nozzle geometry which is similar to the geometry shown in FIG. 21 except that the divergence extends over a very short length longitudinally, as shown in FIG. 25. The divergence typically covers a longitudinal length "A" of only one quarter to one eighth of the diameter of the second convergence 9 and this nozzle geometry is referred to as a "fast expand" nozzle. The idea behind it is that the gas should be expanded as quickly as possible so as to ensure that particles are accelerated by the fast moving gas stream for the longest time period possible. This is thought to provide a higher particle speed. The "fast expand" nozzle may be used to replace the nozzle of any of the previously described embodiments.

Examples of Performance of Some Embodiments

The device shown in FIG. 20 having a 10 mm nozzle exit diameter has been tested with different volumes (3 and 5 ml) and driver pressures (20 to 60 bar). In general, low driving pressures (5 ml at 25 bar) give very uniform distribution of the particles on the target but with relatively low penetrations (160 to 180 μm) of 47 μm diameter polystyrene beads into a 3% agar gel target. As the driver pressure is increased, the penetration increases but the particle distribution becomes more skewed to that side of the target which is opposite the position of powder entry via the particle inlet passage 10. Further increase of the gas pressure causes the pressure in the chamber 8 to rise above that of the atmosphere which results in the particles being ejected from the air aspiration hole. This problem was overcome by increasing the diameter of the upstream parallel exit nozzle section to accommodate the higher gas flow rates.

Mass flow rates (and particle penetration) were also increased by using larger diameter sonic throats. In this embodiment, which utilizes the outside atmospheric pressure to draw in the particle payload, it is necessary to ensure that the sonic throat and parallel section of the diameters are matched, to prevent a blow-back of particles. The alignment of the sonic throat exit plane and the particle inlet passage 10 in the chamber 8 is also important in preventing the particle blow-back.

Figure 26:
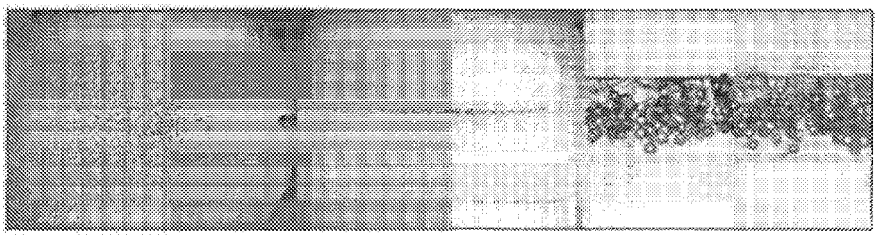
FIG. 26 shows a top plan view of the target area of a gel target, a side cross-sectional view of the target and an enlarged side cross-sectional view of the gel target after the firing at it of particles from the syringe of FIG. 20.

A 10 mm diameter exit plane device, fitted with a 1.2 mm diameter sonic throat and a 3 mm diameter upstream exit nozzle parallel section and using a 5 ml, 40 bar helium canister gave the footprint and penetration results shown in FIG. 26. The payload was 1 mg of 48 μm of polystyrene beads.

The left hand image shows the footprint (approximately 11 mm diameter) of the particles and a 3% agar gel target: there is an increased concentration of particles near the centre of the footprint, but the asymmetry of the distribution is not so noticeable in this image. The middle image shows the distribution of particles across a diametral slice of the target and the left hand image shows an enlarged view of particle penetration at the center of the slice, from which a maximum penetration of 250 μm can be measured.

Noise levels from this device at these conditions were not high (max=81 dBA, linear peak=120 dB, measured at 0.3 meters).

Figure 27:
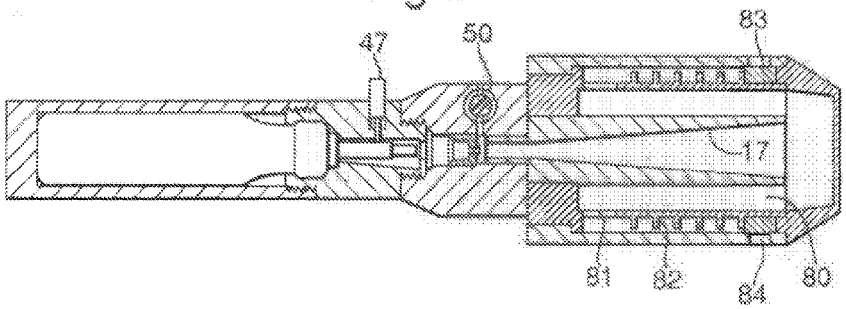
FIG. 27 is a schematic cross-section along the central longitudinal axis of a needleless syringe, showing a silencer arrangement arranged around the exit nozzle.

A simple silencer device (shown in FIG. 27) was fitted to the FIG. 20 embodiment. The silencer consists of a first passage 80 which the gas upon which rebounding from the target plane passes along. This passage 80 is aligned in an annulus around the exit nozzle 17. The gas then passes through a port 81 before being passed across a series of radially extending baffles 82. It is thought the baffles serve to breakdown the gas pressure into a series of shock waves. Finally, the gas passes through a mesh filter 83 and out through an exit port 84.

This arrangement produced significantly lower noise levels (max=73 dBA, linear peak=109 dB at 0.3 meters). Use of the silencer produces a back pressure which has two effects. The first effect is to generate a "lift-off" force which tends to separate the device from the target plane and the second effect is to reduce the performance of the device, since the gas is now expanded to a nozzle exit pressure above atmospheric.

The lift-off force of the silenced device was measured by operating it against a flat plate loaded with different masses, a displacement transducer indicating when the sealing force was insufficient to maintain contact. This method gave lift-off forces of the order of 5 N, which is considerably lower than the Fig. obtained by assuming that the peak pressure maintained on the plate generates the maximum lift-off force (13 N).

Figure 28:
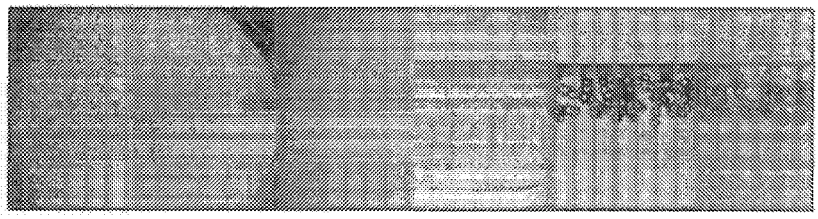
FIG. 28 is a top plan view of the target area of the gel target, a side cross-sectional view through the gel target and an enlarged side cross-sectional view through the gel target after the firing at it of particles from the syringe shown in FIG. 27.

FIG. 28 shows the same data for the silenced device as that displayed in FIG. 26 for the unsilenced device. The main difference is that the maximum penetration has been reduced to 225 μm.

The device shown in FIG. 21 was also tested. This device also has a 10 mm diameter exit plane and the downstream parallel extension 65 is 30 mm long.

Figure 29:
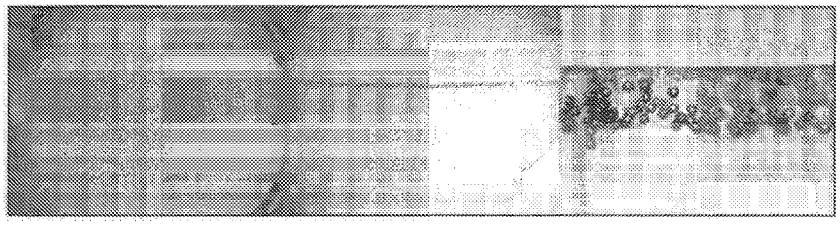
FIG. 29 is a top plan view of the target area of the gel target, a side cross-sectional view through the gel target and an enlarged side cross-sectional view through the gel target after the firing at it of particles from the syringe shown in FIG. 21.
Figure 30:
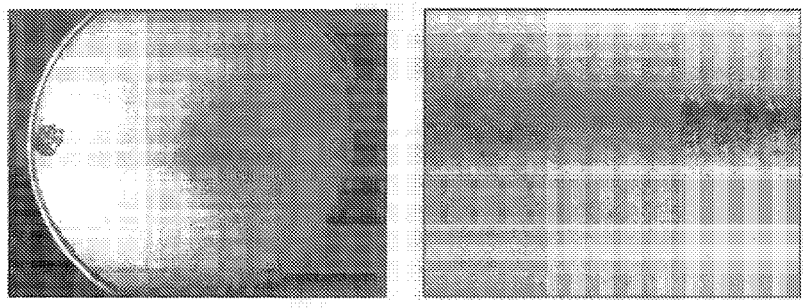
FIG. 30 is a top plan view of the target area of the gel target, a side cross-sectional view through the gel target and a graph showing the penetration depth variation with position after the firing at the gel target of particles from the needleless syringe shown in FIG. 20.
Figure 30:
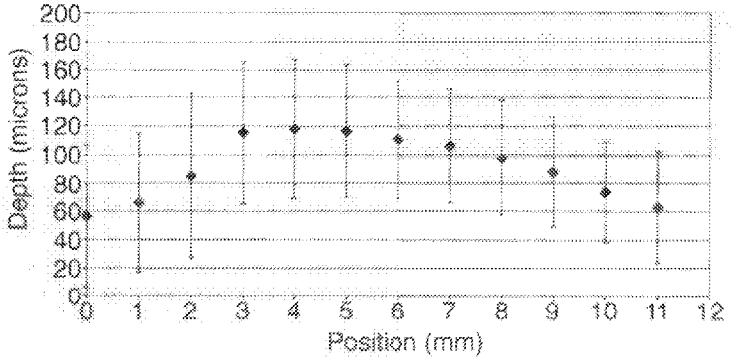

FIG. 29 shows the improved footprint achieved when this device was operated at conditions corresponding to those of FIG. 26. The particles are more uniformly dispersed over the target and the maximum penetration is still 250 μm. The measured noise levels in this case were max=79.3 dBA, linear peak=119.4 dB. The device of FIG. 20 was also tested with a 0.6 mg payload of 50 R gold particles (mean diameter=1.8 μm). The sonic throat was increased to 1.3 mm and used with a 50 bar, 5 ml helium cylinder. The footprint and mean penetrations are shown in FIG. 30.

It can be seen from the Figures that the particles are fairly asymmetrically distributed on the target and that the distribution of penetration depths is large—ranging from 60 μm at the edges to 120 μm near the center.

Figure 31:
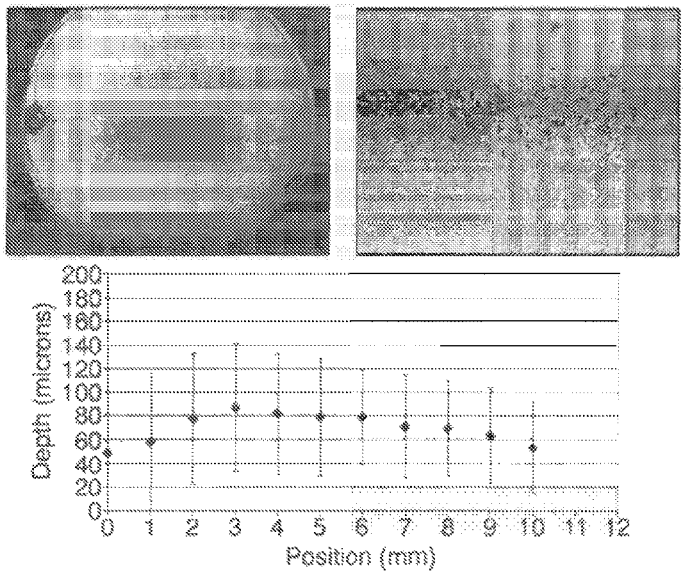
FIG. 31 is a top plan view of the target area of the gel target, a side cross-sectional view through the gel target and a graph showing the penetration depth variation with position after the firing at the gel target of particles from the needleless syringe shown in FIG. 21.

A 30 mm parallel extension as shown in FIG. 21 was added to the device and the results are shown in FIG. 31. As can be seen, matters were not particularly improved since the mean penetration depths are now lower, the asymmetric distribution is still evident and the variation in depth of the particles has increased.

Figure 32:
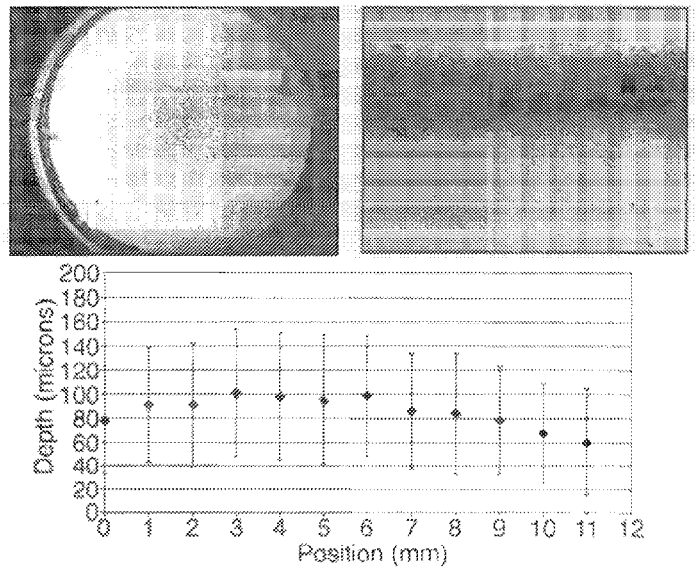
FIG. 32 is a top plan view of the target area of the gel target, a side cross-sectional view through the gel target and a graph showing the penetration depth variation with position after the firing at the gel target of particles from the needleless syringe shown in FIG. 21.

An improved distribution and penetration was achieved by adding gold particles to larger diameter lidocaine powder in the powder cassette. The gold particles were sandwiched between two layers of lidocaine. The results are shown in FIG. 32 where it can be seen that the lidocaine particles caused some damage to surface of the agar gel target, but dissolved rapidly to leave the gold particles behind.

Figure 33:
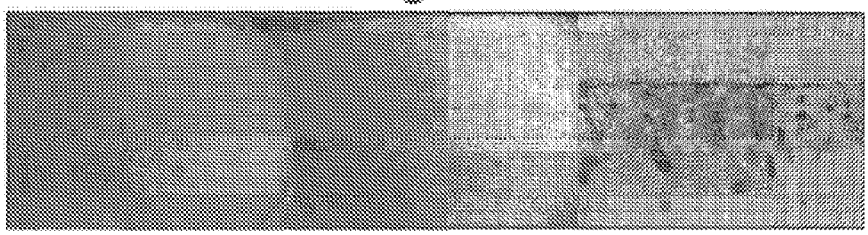
FIG. 33 is a top plan view of the target area of the gel target, a side cross-sectional view through the gel target and an enlarged side cross-sectional view through the gel target respectively, after the firing at it of particles from the syringe shown in FIG. 21.

The most powerful version of the FIG. 20 device tested had a 1.4 mm diameter sonic throat, a 3.5 mm diameter upstream exit nozzle section and used a 60 bar, 5 ml helium cannister. When used with a payload of 1 mg of polystyrene spheres, it produced a crater in the centre of the 3% agar gel target. With the 30 mm parallel extension (FIG. 21) there was comparatively little damage to the target. An example of the performance of the device is shown in FIG. 33 where the target is a 3% agar gel and the payload was 1 mg of 50 μm agarose beads (A-121). These particles have a lower density than either polystyrene or lidocaine and consequently they do not penetrate as deeply for a given velocity. Nevertheless, the maximum penetration measured was 280 μm.

Figure 34:
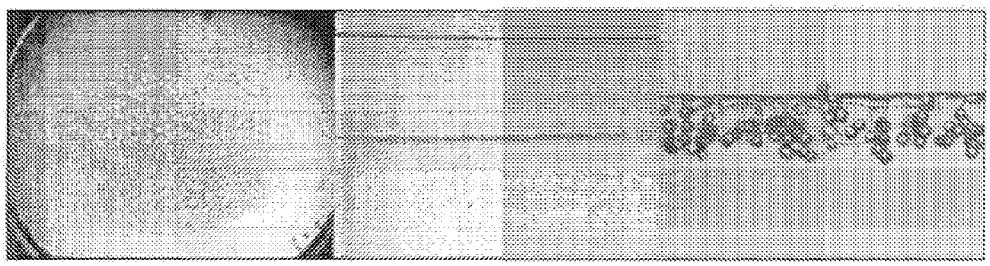
FIG. 34 is a top plan view of the target area of a gel target, a side cross-sectional view through the gel target and an enlarged side cross-sectional view through the gel target after the firing at it of particles from the syringe shown in FIG. 20.

FIG. 34 shows the results when the device of FIG. 20 was used with a 1 mg payload of particles and a driver pressure of 25 bar. As can be seen, a maximum penetration of 120 μm and a footprint of about 11 mm diameter was obtained.

It may be advantageous to provide a high efficiency particle air filter so as to remove any potential source of contamination from air drawn into the syringe through the cassette of the particle source. Such filters are commercially available and have low pressure drops. Such filters have an upper limit to gas velocity through the filter so as to ensure that they operate to the specification. The surface area of such a filter could clearly be chosen to match the gas velocity therethrough that will be encountered in use.

An alternative to an air filter would be to bleed a supply of driver gas at, or near, atmospheric pressure to the particle cassette inlet. As described above with relation to the seventh embodiment, however, the gas bled to the particle inlet may be substantially higher than atmospheric.

Although the above described embodiments were used for single dose operation, they may readily be modified to make them suitable for multiple dose operation, for example by providing them with a plurality of gas canisters and modifying the cassette of the particle source 11 to contain a plurality of discrete particle reservoirs 12, each of which can be indexed to align with the particle inlet passage 10 between successive shots.

Any of the already described nozzles may be contoured, for example, using the method of characteristics, to provide a reduction in the number of oblique shock waves that form in the nozzle during use. Profiling the nozzle in this way is also thought to improve the particle distribution at the exit plane.

For some use locations, such as surgeries, operating theaters and the like, in which connection of the syringe to a supply of gas using a flexible hose, for example, would be acceptable, multiple operation of the device could well be possible using a simple push-pull valve arrangement to fire the syringe.

The major components of the needleless syringe (main housing, sonic nozzle, nozzle barrel etc) may for example be made of metal or of engineering plastics materials. The latter materials are preferred because they may readily be molded and are light in weight.

Although the device of all embodiments of the present invention is designed to be quieter in operation than the device of U.S. Pat. No. 5,630,796 (which uses a rupturable membrane), some noise is still detected and a silencing device, perhaps comprising a plurality of baffles and a mesh filter can be used to further reduce the noise experienced.

The present invention is primarily concerned with the reduction of noise and improved uniform particle spread that can be achieved by using the Venturi effect to draw the particles into the gas flow path. However, the Venturi effect is not essential for this purpose and other methods of introducing the particles into the flow may be utilized. For example, the particles may be initially lightly adhered to the inside of a tubular member which is initially provided in the gas flow path. Upon actuation, the gas flow is able to shear the particles from the tube and thereby entrain them.

The invention claimed is:

1. A needleless syringe for use in the needleless injection of particles into the skin of a vertebrate subject, the syringe comprising:

a gas flow path arranged to receive gas from a gas source;

a first convergence in said gas flow path for reducing the pressure of the gas flowing through said gas flow path;

a particle inlet for introducing particles into said gas flow separately from the gas, said particle inlet being in communication with said gas flow path downstream of at least the start of said first convergence so as to allow a payload of particles to be drawn into the gas flow path via the particle inlet under the action of reduced pressure gas to become entrained in the gas;

a gas/particle exit nozzle [bounding said gas flow path for the acceleration of the drawn in particles entrained in the gas]; and a powder chamber, containing at least one payload of particles, in communication with the particle inlet so as to enable the particles of a payload to be drawn into the gas flow path from said powder chamber along the passage of said particle inlet, wherein said powder chamber is configured to be moved so as to bring said particle payload into and out of communication with said particle inlet.

2. A syringe according to claim 1, further comprising a chamber of increased cross-section downstream of said convergence and bounding said gas flow path such that, in use, a transsonic gas jet is formed in said chamber.

3. A syringe according to claim 2, wherein said particle inlet is positioned relative to said chamber so that the particles are drawn, in use, into the chamber.

4. A syringe according to claim 3, wherein the nozzle is provided at its upstream end with a gas and particle inlet for the flow therethrough into the nozzle of the drawn-in particles entrained in the gas jet, said gas and particle inlet comprising a second convergence of reduced flow cross-section relative to the flow cross-section of the chamber.

5. A syringe according to claim 4, wherein the minimum flow cross-section of the second convergence is at least 4 times the area of the minimum flow cross-section of the first convergence.

6. A syringe according to claim 4, wherein the first and second convergences are aligned along a common axis and the particle inlet comprises a passage whose central longitudinal axis is generally transverse to said common axis.

7. A syringe according to claim 1, wherein said gas flow path comprises a divergent section downstream of said convergence.

8. A syringe according to claim 7, wherein said particle inlet is positioned in said divergent section.

9. A syringe according to claim 6, wherein said particle inlet is positioned in said exit nozzle.

10. A syringe according to claim 1, wherein said particle inlet is positioned in said first convergence.

11. A syringe according to claim 1, wherein moving said powder chamber so that said particle payload is in communication with said particle inlet also triggers said syringe.

12. A syringe according to claim 1, wherein said particle inlet is connected or connectable to an upstream region of the gas flow path such that the particles will, in use, be drawn into the gas flow path due to the pressure difference between said upstream region and the gas flow path adjacent the particle inlet.

13. A syringe according to claim 1, wherein the exit nozzle comprises an upstream, parallel-sided section, leading into a divergent section.

14. A syringe according to claim 13, further comprising a passage fluidly connecting a part of said divergent section with a more upstream part of the gas flow path.

15. A syringe as claimed in claim 13, wherein the diameter of the nozzle at its downstream exit is between 2 and 30 mm in diameter.

16. A syringe according to claim 4, wherein said second convergence is an abrupt constriction.

17. A syringe according to claim 1, wherein said first convergence is an abrupt constriction.

18. A syringe according to claim 4, wherein the minimum flow cross-section of the second convergence is at least 5 times the area of the minimum flow cross-section of the first convergence.

19. A syringe as claimed in claim 13, wherein the diameter of the nozzle at its downstream exit is between 3 and 15 mm.

20. A syringe as claimed in claim 13, wherein the diameter of the nozzle at its downstream exit is greater than 5 mm.

21. A syringe as claimed in claim 13, wherein the diameter of the nozzle at its downstream exit is greater than 8 mm.

22. A syringe as claimed in claim 13, wherein the diameter of the nozzle at its downstream exit is greater than 11 mm.

23. A syringe as claimed in claim 1, further comprising a source of compressed gas connected to the upstream end of said gas flow path.

* * * * *